United States Patent
Ailhaud et al.

(10) Patent No.: US 9,790,469 B2
(45) Date of Patent: Oct. 17, 2017

(54) ESTABLISHED HUMAN BROWN ADIPOCYTE LINE AND METHOD FOR DIFFERENTIATION FROM AN HMADS CELL LINE

(75) Inventors: Gérard Paul Ailhaud, Gonfaron (FR); Ez-Zoubir Amri, Nice (FR); Christian Jean Lucien Dani, Nice (FR); Christian Elabd, Nice (FR)

(73) Assignees: CENTRE NATIONAL DE LA RECHERCHE SCIENTIFIQUE (CNRS), Paris (FR); UNIVERSITE DE NICE SOPHIA-ANTIPOLIS, Nice (FR)

( * ) Notice: Subject to any disclaimer, the term of this patent is extended or adjusted under 35 U.S.C. 154(b) by 634 days.

(21) Appl. No.: 13/000,904

(22) PCT Filed: Jun. 23, 2009

(86) PCT No.: PCT/EP2009/057852
§ 371 (c)(1),
(2), (4) Date: Dec. 22, 2010

(87) PCT Pub. No.: WO2009/156413
PCT Pub. Date: Dec. 30, 2009

(65) Prior Publication Data
US 2011/0117066 A1    May 19, 2011

(30) Foreign Application Priority Data
Jun. 23, 2008  (FR) ...................... 08 54140

(51) Int. Cl.
*C12N 5/0775* (2010.01)
*G01N 33/50* (2006.01)

(52) U.S. Cl.
CPC ....... *C12N 5/0667* (2013.01); *G01N 33/5044* (2013.01); *C12N 2501/115* (2013.01); *C12N 2501/385* (2013.01); *C12N 2501/39* (2013.01); *C12N 2501/81* (2013.01)

(58) Field of Classification Search
USPC ......................................... 435/377; 424/93.7
See application file for complete search history.

(56) References Cited

U.S. PATENT DOCUMENTS

| | | | | |
|---|---|---|---|---|
| 6,071,747 A * | 6/2000 | Strosberg | ................ | C07K 16/18 435/366 |
| 2003/0229204 A1* | 12/2003 | Spiegelman et al. | ......... | 530/350 |
| 2005/0187154 A1* | 8/2005 | Kahn | ................. | A61K 38/1709 514/4.8 |
| 2009/0169642 A1* | 7/2009 | Fradette et al. | .............. | 424/574 |
| 2011/0104133 A1* | 5/2011 | Tseng et al. | ............... | 424/93.21 |

OTHER PUBLICATIONS

Tiraby (J. Biol. Chem., 2003, vol. 278, No1. 35, 33370-33376).*
Rodriguez, Anne-Marie et al. Transplantation of a Multipotent Cell Population from Human Adipose tissue Induces Dystrophin Expression in the Immunocompetent MDX Mouse. The Journal of Experimental Medicine vol. 201, No. 9. May 2, 2005. pp. 1397-1405.*
Bunnell, Bruce et al. Adipose-derived Stem Cells: Isolation, Expansion and Differentiation. Methods. Jun. 2008; 45(2): 115-120. doi:10.1016/j.ymeth.2008.03.006.*
Rodriguez, Anne-Marie et al. Adipocyte Differentiation of Multipotent Cells Established from Human Adipose Tissue. Biochemical and Biophysical Research Communications 315 (2004). Elsevier. pp. 255-263.*
Rodriguez (Adipocyte Differentiation of Multipotent Cells Established from Human Adipose Tissue, 2004).*
Roche (Insulin-Transferrin-Sodium Selenite Supplement, 2004).*
Bunnell, Bruce. Adipose-derived Stem Cells: Isolation, Expansion and Differentiation. Methods. Jun. 2008 ; 45(2): 115-120.*
Digby et al., "Depot-related and thiazolidinedione-responsive expression of uncoupling protein 2 (UCP2) in human adipocytes", International Journal of Obesity, vol. 24, 2000, pp. 585-592.
Digby et al., "Thiazolidinedione Exposure Increases the Expression of Uncoupling Protein 1 in Cultured Human Preadipocytes", Diabetes, vol. 47, Jan. 1998, pp. 138-141.
Elabd et al., "Human Multipotent Adipose-Derived Stem Cells Differentiate into Functional Brown Adipocytes", Stem Cells, vol. 27, 2009, pp. 2753-2760.
Ailhaud et al., "Cellular and Molecular Aspects of Adipose Tissue Development", Annu. Rev. Nutr., vol. 12, pp. 207-233, 1992.
Bezy et al., "Delta-interactiong Protein A, a New Inhibitory Partner of CCAAT/Enhancer-binding Protein β, Implicated in Adipocyte Differentiation", The Journal of Biological Chemistry, vol. 280, No. 12, pp. 11432-11438, Mar. 25, 2005.
Bogacka et al., "Pioglitazone Induces Mitochondrial Biogenesis in Human Subcutaneous Adipose Tissue in Vivo", Diabetes, vol. 54, pp. 1392-1399, May 2005.
Briscini et al., "Bcl-2 and Bax are involved in the sympathetic protection of brown adipocyte from obesity-linked apoptosis", FEBS Letters, vol. 431, pp. 80-84, 1998.
Cannon et al., "Brown Asipose Tissue: Function and Physiological Significance", Physiol Rev, vol. 84, pp. 277-359, 2004.
Carmona et al., "Fenofibrate prevents Rosiglitazone-induced body weight gain in ob/ob mice", International Journal of Obesity, vol. 29, pp. 864-871, May 10, 2005.

(Continued)

*Primary Examiner* — Scott Long
*Assistant Examiner* — Nghi Nguyen
(74) *Attorney, Agent, or Firm* — Birch, Stewart, Kolasch & Birch, LLP

(57) ABSTRACT

The subject matter of the invention is a functional population of human brown adipocytes, in which the expression of UCP1, CIDEA, CPT1B and Bcl2 is higher, the expression of Bax is lower and the expression of PPAR-alpha, PGC-1alpha, PGC-1 beta and PRDM16 is similar compared with the corresponding expressions of a population of human white adipocytes. The invention also relates to a method for differentiation of hMADS cells into the functional population of human brown adipocytes, to a method for conversion of a population of human white adipocytes into the functional population of human brown adipocytes, and also to a method of screening for molecules capable of modulating the bodyweight in an individual.

18 Claims, 7 Drawing Sheets

(56) References Cited

OTHER PUBLICATIONS

Casteilla et al., "Characterization of mitochondrial-uncoupling protien in bovine fetus and newborn calf. Disappearace in lamb during aging.", The American Physiological Society, pp. E627-E636, 1987.

Casteilla et al., "Differentiation of ovine brown adipocyte precursor cells in a chemically defined serum-free medium", Eur. J. Biochem., vol. 198, pp. 195-199, 1991.

Casteilla et al., "Sequential changes in the expression of mitochondrial protein mRNA during the development of brown adipose tissue in bovine and ovine species", Biochem., vol. 257, pp. 665-671, 1989.

Cinti, "The role of brown adipose tissue in human obesity", Nutrition, Metabolism & Cardiovascular Diseases, vol. 16, pp. 569-574, 2006.

Cousin et al., "Occurence of brown adipocytes in rat white adipose tissue: molecular and morphological characterization", Journal of Cell Science, vol. 103, pp. 931-942, 1992.

Elabd et al., "Human adipose tissue-derived multipotent stem cells differentiate in vitro and in vivo into osteocyte-like cells", Biochemical and Biophysical Research Communications, vol. 361, pp. 342-348, 2007 (Available online Jul. 20, 2007).

Farmer, "Molecular determinants of brown adipocyte formation and function", Genes & Developement, vol. 22, pp. 1269-1275, 2008, XP-002505377.

Foellmi-Adams et al., "Induction of Uncoupling Protein in Brown Adipose Tissue", Biochemical Pharmacology, vol. 52, pp. 693-701, 1996.

Forman et al., "15-Deoxy-Δ12, 14-Prostaglandin J2 Is a Ligand for the Adipocyte Determination Factor PPARγ", Cell, vol. 83, pp. 803-812, Dec. 1, 1995.

French Preliminary Search Report dated Nov. 26, 2008, for Application No. 0854140.

Fukui et al., "A New Thiazolidinedione, NC-2100, Which Is a Weak PPAR-γ Activator, Exhibits Potent Antidiabetic Effects and Induces Uncoupling Protein 1 in White Adipose Tissue of KKAy Obese Mice", Diabetes, vol. 49, pp. 759-767, May 2000.

Garruti et al., "Analysis of uncoupling protein and its mRNA in adipose tissue deposits of adult humans", International Journal of Obesity, vol. 16, pp. 383-390, 1992.

Goldberg, "The new clinical trials with thiazolidinediones—Dream, Adopt, and Chicago: promises fulfilled?", Current Opinion in Lipidology, vol. 18, pp. 435-442, 2007.

Home et al., "Rosiglitazone Record study: glucose control outcomes at 18 months", Diabetic Medicine, vol. 24, pp. 626-634, 2007.

International Search Report dated Aug. 14, 2009 for Application No. PCT/EP2009/057852.

Jockers et al., "Desensitization of the β-Adrenergic Response in Human Brown Adipocytes", Endocrinology, vol. 139, No. 6, pp. 2676-2684, 1998.

Joosen et al., "The effect of the PPARγ ligand rosiglitazone on energy balance regulation", Diabetes/Metabolism Research and Reviews, vol. 22, pp. 204-210, 2006 (Published online Aug. 19, 2005).

Kang et al., "Effects of Wnt Signaling on Brown Adipocyte Differentiation and Metabolism Mediated by PGC-1α", Molecular and Cellular Biology, vol. 25, No. 4, pp. 1272-1282, Feb. 2005.

Kelly et al., "Peroxisome Proliferator-Activated Peceptors γ and α Mediate in Vivo Regulation of Uncoupling Protein (UCP-1, UCP-2, UCP-3) Gene Expression", Endocrinology, vol. 139, No. 12, pp. 4920-4927, 1998.

Lafontan et al., "Do regional differences in adipocyte biology provide new pathophysiological insights?", Trends in Pharmacological Sciences, vol. 254, No. 6, pp, 276-283, Jun. 2003.

Lindquist et al., "Ambient Temperature Regulation of Apoptosis in Brown Adipose Tissue", The Journal of Biological Chemistry, vol. 273, No. 46, pp. 30147-30156, Nov. 13, 1998.

Lowell et al., "Development of obesity in trangenic mice after genetic ablation of brown adipose tissue", Nature, vol. 366, pp. 740-742, Dec. 23-30, 1993.

Lowell et al., "β-Adrenergic Receptors, Diet-induced Thermogenesis, and Obesity", The Journal of Biological Chemistry, vol. 278, No. 32, pp. 29385-29388, Aug. 8, 2003.

Mercer et al., "Effects of ciglitazone on insulin resistance and thermogenic responsiveness to acute cold in brown adipose tissue of genetically obese (ob/ob) mice", FEBS 3249, vol. 195, No. 1,2, pp. 12-16, Jan. 1986.

Moulin et al.,"Emergence during development of the white-adipocyte cell phenotype is independent of the brown-adipocyte cell phenotype", Biochem. J., vol. 356, pp. 659-664, 2001.

Nedergaard et al., "PPARγ in the control of brown adipocyte differentiation", Biochemica et Biophysica Acta , vol. 1740, pp. 293-304, 2005 (Available online Mar. 17, 2005).

Nedergaard et al., "Unexpected evidence for active brown adipose tissue in adult humans", Am J Endocrinol Metab, vol. 293, pp. E444-E452, May 1, 2007.

Négrel et al., "Establishment of preadipocyte clonal line from epididymal fat pad of ob/ob mouse that responds to insulin and to lipolytic hormones", Proc. Natl. Acad. Sci. USA, vol. 75, No. 12, pp. 6054-6058, Dec. 1978.

Nisoli et al., "White adipocytes are less prone to apoptotic stimuli than brown adipocytes in rodent", Cell and Death Differentiation, vol. 13, pp. 2154-2156, 2006.

Olefsky et al., "PPARγ and the Treatment of Insulin Resistance", TEM, vol. 11, No. 9, pp. 362-368, 2000.

Papineau et al., "Apoptosis of Human Abdominal Preadipocytes Before and After Differentiation Into Adipocytes in Culture", Metabolism, vol. 52, No. 8, pp. 987-992, Aug. 2003.

Petrovic, "Thermogenically competent nonadrenergic recruitment in brown preadipocytes by a PPARγ agonist", Am J Physiol Endcrinol Metab, vol. 295, pp. E287-E296, May 20, 2008.

Puigserver et al., "Cytokine Stimulation of Energy Expenditure through p38 MAP Kinase Activation of PPARγ Coactivator-1", Molecular Cell, vol. 8, Nov. 2001, pp. 971-982.

Rodriguez et al., "Adipocyte differentiation of multipotent cells established from human adipose tissue", Biochemical and Biophysical Research Communications, vol. 315, pp. 255-263, 2004.

Rodriguez et al., "The human adipose tissue is a source of multipotent stem cells", Biochimie, vol. 87, pp. 125-128, 2005.

Rodriguez et al., "Transplantation of a multipotent cell population from human adipose tissue induces dystrophin expression in the immunocompetent mdx mouse", The Journal of Experimental Medicine, vol. 201, No. 9, pp. 1397-1405, May 2, 2005.

Rosen et al., "Adipocytes as regulators of energy balance and glucose homeostasis", Nature, vol. 444, pp. 847-853, Dec. 14, 2006.

Seale et al., "Transcriptional Control of Brown Fat Determination by PRDM16", Cell Metab., vol. 6, No. 1, pp. 38-54, Jul. 2007.

Tai et al., "Activation of the Nuclear Receptor Peroxisome Proliferator-activated Receptor γ Promotes Brown Adipocyte Differentiation", The Journal of Biological Chemistry, vol. 271, No. 47, pp. 29909-29914, Nov. 22, 1996.

Timmons et al., "Myogenic gene expression signature establishes that brown and white adipocytes originate from distinct cell lineages", PNAS, vol. 104, No. 11, pp. 4401-4406, Mar. 13, 2007.

Tiraby et al., "Acquirement of Brown Fat Cell Features by Human White Adipocytes", The Journal of Biological Chemistry, vol. 278, No. 35, pp. 33370-33376, Aug. 29, 2003.

Tiraby et al., "Conversion from white to brown adipocytes: a strategy for the control of fat mass?", Trends in Endocrinology and Metabolism, vol. 14, No. 10, Dec. 2003.

Uldry et al., "Complementary action of the PGC-1 coactivators in mitochondrial biogenesis and brown fat differentiation", Cell Metabolism, vol. 3, pp. 333-341, May 2006.

Viguerie-Bascands et al., "Evidence for Numerous Brown Adipocytes Lacking Functional β3-Adrenoceptors in Fat Pads From Nonhuman Primates", Journal of Clinical Endocrinology and Metabolism, vol. 81, No. 1, pp. 368-375, 1996.

(56) References Cited

OTHER PUBLICATIONS

Viswakarma et al., "Transcriptional Regulation of Cidea, Mitochondrial Cell Death-inducing DNA Fragmentation Factor α-Like Effector A, in Mouse Liver by Peroxisome Proliferator-activated Receptor α and γ", The Journal of Biological Chemistry, vol. 282, No. 25, pp. 18613-18624, Jun. 22, 2007.

Watanabe et al., "Bile acids induce energy expenditure by promoting intracellular thyroid hormone activation", Nature, vol. 439, pp. 484-489, Jan. 26, 2006.

Wilson-Fritch et al., "Mitochondrial Biogenesis and Remodeling during Adipogenesis and in Response to the Insulin Sensitizer Rosiglitazone", Molecular and Cellular Biology, vol. 23, No. 3, Feb. 2003, pp. 1085-1094, XP-002505381.

Wilson-Fritch et al., "Mitochondrial remodeling in adipose tissue associated with obesity and treatment with rosiglitazone", The Journal of Clinical Investigation, vol. 114, No. 9, pp. 1281-1289, Nov. 2004.

Xue et al., "Transcriptional Synergy and the Regulation of Ucp1 during Brown Adipocyte Induction in White Fat Depots", Molecular and Cellular Biology, vol. 25, No. 18, pp. 8311-8322, Sep. 2005.

Zaragosi et al., "Autocrine Fibroblast Growth Factor 2 Signaling Is Critical for Self-Renewal of Human Multipotent Adipose-Derived Stem Cells", Stem Cells, vol. 24, pp. 2412-2419, 2006 (Published online Jul. 13, 2006).

Zhou et al., "Cidea-deficient mice have lean phenotype and are resistant to obesity", Nature Genetics, vol. 35, No. 1, pp. 49-56, Sep. 2003 (Published online Aug. 10, 2003).

Zilberfarb et al., "Human immortalized brown adipocytes express functional β3-adrenoceptor coupled to lipolysis", Journal of Cell Science, vol. 110, pp. 801-807, 1997.

\* cited by examiner

ESTABLISHED HUMAN BROWN ADIPOCYTE LINE AND METHOD FOR DIFFERENTIATION FROM AN HMADS CELL LINE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM 9EFS-WEB)

Not Applicable

STATEMENT REGARDING PRIOR DISCLOSUREWS BY THE INVENTOR OR A JOINT INVENTOR

Not Applicable

BACKGROUND OF THE INVENTION

Field of the Invention

The invention relates to a functional human brown adipocytes population, in which the expression of UCP1, CIDEA, CPT1B and Bcl-2 is higher, the expression of Bax is lower, and the expression of PPARα, PGC-1α, PGC-1β and PRDM16 is similar compared with the corresponding expressions of a human white adipocytes population. The invention also relates to a method for differentiating hMADS cells into the functional human brown adipocytes population, a method for converting a human white adipocytes population into the functional human brown adipocytes population, and a screening method for molecules capable of modulating the body weight in an individual.

Description of Related Art including information disclosed under 37 CFR 1.97 and 1.98

White adipose tissue (WAT) plays a key role in humans in the control of energy balance and carbohydrate-lipid homeostasis (Ailhaud G. et al., Annu Rev Nutr, 1992. 12: p. 207-233; Rosen, E. D. and B. M. Spiegelman, Nature, 2006. 444(7121): p. 847-53). As opposed to WAT, brown adipose tissue (BAT) is specialized in adaptive thermogenesis during which the uncoupling protein UCP1 plays a decisive role. The presence of brown adipose tissue is well known in rodents as in larger newborn mammals (Garruti, G. and D. Ricquier, Int J Obes Relat Metab Disord, 1992. 16(5): p. 383-90; Cannon, B. and J. Nedergaard, Physiol Rev, 2004. 84(1): p. 277-359). A particularly striking fact is that recent data suggest the existence of functional BAT in healthy adult humans (Nedergaard, J. et al., Am J Physiol Endocrinol Metab, 2007. 293(2): p. E444-52; Cypess, A M et al., N. Engl. J. Med. 2009. 360: p. 1509-17; Saito, M. et al., Diabetes 2009. Published Ahead of Print, Online April 28; van Marken Lichtenbelt, W et al., N. Engl. J. Med. 2009. 390: p. 1500-08; Virtanen, K A et al., N. Engl. J. Med. 2009. 360: p. 1518-1525).

In vivo, the appearance in rodents of brown adipocytes islets in the middle of WAT deposits is known (Timmons, J. A., et al., Proc Natl Acad Sci USA, 2007. 104(11): p. 4401-6; Cousin, B., et al., J Cell Sci, 1992. 103 (Pt 4): p. 931-42; Xue, B., et al., Mol Cell Biol, 2005. 25(18): p. 8311-22), following an exposure to cold or a treatment with β-adrenergic receptor (β-AR) agonists. Similarly, after a treatment with PPARγ agonistic ligands, the appearance of cells expressing UCP1 in white adipose deposits was also documented in rodents and in human (Wilson-Fritch, L., et al., J Clin Invest, 2004. 114(9): p. 1281-9; Fukui, Y., et al., Diabetes, 2000. 49(5): p. 759-67; Bogacka, I., et al., Diabetes, 2005. 54(5): p. 1392-9). However, these observations cannot exclude the prior existence of brown precursors in such sites. Reciprocally, the rapid conversion of BAT into WAT in human newborns as in ovine and bovine newborns cannot exclude the prior existence of white precursors (Casteilla, L., et al., Am J Physiol, 1987. 252(5 Pt 1): p. E627-36; Casteilla, L., et al., Biochem J, 1989. 257(3): p. 665-71; Casteilla, L., et al., Eur J Biochem, 1991. 198(1): p. 195-9). The existence of a precursor cell common to white and brown lines remains to be shown, insofar as the pre-adipocytes obtained ex vivo from WAT and BAT give only rise to white and brown adipocytes, respectively (Moulin, K., et al., Biochem J, 2001. 356(Pt 2): p. 659-64). Recent work in the mouse supports this possibility by showing the existence of a myogenic transcriptome signature of brown adipocytes distinct from that of white adipocytes (Timmons, J. A., et al., Proc Natl Acad Sci USA, 2007. 104(11): p. 4401-6).

However, other work underlines the possibility to generate brown adipocytes from white adipocytes by transgenesis (Tiraby, C. and D. Langin, Trends Endocrinol Metab, 2003. 14(10): p. 439-41; Tiraby, C, et al., J Biol Chem, 2003. 278(35): p. 33370-6) and several co-activators and transcription factors take part in the formation of brown adipocytes. Thus, during differentiation PGC-1α and PGC-1β play an essential and complementary role in mitochondriogenesis and respiration (Puigserver, P., et al., Mol Cell, 2001. 8(5): p. 971-82; Uldry, M., et al., Cell Metab, 2006. 3(5): p. 333-41). However, contrary to these PPARγ coactivators, the zinc finger transcription protein PRDM16 truly controls the "brown" determination of white preadipocytes by induction of PGC-1α, UCP1 and type II iodothyronine deiodinase (Dio2) (Seale, P., et al., Cell Metab, 2007. 6(1): p. 38-54).

The article by Zilberfarb et al., 1997, J Cell Sci 110(Pt 7), 801-807, describes an immortalized line of human brown adipocytes, PAZ6, which is obtained by transgenesis. This article shows that the PAZ6 line expresses mRNA coding for UCP1.

However, it does not show that this expression leads to a functional UCP1, i.e., one that has uncoupling activity due to its location in the inner mitochondrial membrane, thus conferring to the human brown adipocytes a respiratory activity and an uncoupling activity that are significantly higher than those of human white adipocytes. Moreover, no stimulation of respiratory activity by a specific agonist of β-adrenergic receptors is reported as being dependant on the presence of UCP1.

Moreover, the article by Zilberfarb et al., 1997 describes that the β3-adrenergic receptor is coupled with adenylate cyclase and with lipolysis in PAZ6 cells. This coupling between β3-adrenergic receptor and adenylate cyclase is known to be preliminary to a cascade of events leading to the uncoupling activity of UCP1.

However, the article by Zilberfarb et al., 1997 also describes that similar results of coupling between adenylate cyclase and β3-adrenergic receptor have been obtained by other authors (Murphy at al., 1993) by using freshly isolated rat adipocytes. These are in fact white adipocytes (see Murphy et al., 1993: "Correlation of β3-adrenoreceptor-induced activation of cyclic AMP dependent protein kinase with activation of lipolysis in rat white adipocytes").

Thus, the results obtained and described in Zilberfarb et al., 1997 with brown PAZ6 adipocytes are similar to those obtained with white adipocytes, which inevitably leads to a respiratory activity and an uncoupling activity from these brown adipocytes similar to those of white adipocytes. The brown PAZ6 adipocytes described in Zilberfarb et al., 1997 are thus not functional in the context of the present invention.

Recently we have isolated mesenchymatous stem sells (human multipotent adipose-derived stem cells, or hMADS cells) from human adipose tissue. In the clonal state, these cells have a normal karyotype, a strong self-renewal capacity, and an absence of tumorigenicity. hMADS cells prove to be capable of differentiating into several lineages, in particular osteoblastic and adipocytic, and lead in vivo to a bone and muscle regeneration (Rodriguez, A. M., et al., Biochem Biophys Res Commun, 2004. 315(2): p. 255-63; Rodriguez, A. M., et al., J Exp Med, 2005. 201 (9): p. 1397-405; Zaragosi, L. E., et al., Stem Cells, 2006. 24(11): p. 2412-9; Elabd, C., et al., Biochem Biophys Res Commun, 2007. 361(2): p. 342-8). Once differentiated into adipocytes, hMADS cells acquire the functional properties of human white adipocytes (secretion of leptin and adiponectin, responses to insulin and to β-adrenergic agonists and, specific to primates, to atrial natriuretic factor, Rodriguez, A. M., et al., Biochem Biophys Res Commun, 2004. 315(2): p. 255-63). hMADS cells thus represent a suitable cellular model to study their possible capacity to also differentiate into brown adipocytes.

Our results show that a prolonged chronic activation of PPARγ is sufficient to promote their conversion in vitro and to increase their respiratory and uncoupling capacities, and that β-adrenergic receptor agonists, including β3 agonists, positively modulate the expression of UCP1 as well as the stimulation of respiratory activity by a specific agonist of β-adrenergic receptors such as isoproterenol. The differentiation of hMADS cells leads to a functional human brown adipocytes population which can be used as a cellular model, notably to identify molecules capable of modulating body weight, and in particular to treat excess weight and/or obesity.

BRIEF SUMMARY OF THE INVENTION

Thus, according to a first aspect, the present invention relates to a functional human brown adipocytes population which simultaneously expresses the following genes:
the genes encoding the UCP1, CIDEA, CPT1B and Bcl-2 proteins, the expression of these genes being higher than the one of a human white adipocytes population,
the gene encoding the Bax protein, the expression of this gene being lower than the one of a human white adipocytes population, and
the genes encoding the PPARα, PGC-1α, PGC-1β and PRDM16 proteins, the expression of these genes being similar to the one of a human white adipocytes population.

The functional population (or line) of human brown adipocytes according to the present invention arises from a population (or line) of human multipotent adipose-derived stem cells (hMADS cells). The hMADS cells are described in particular in the international application WO 2004/013 275 published Feb. 12, 2004, and in Rodriguez, A. M., et al., Biochem Biophys Res Commun, 2004. 315(2): p. 255-63. These hMADS cells are capable to differentiate into various cell types such as adipocytes, osteoblasts, myocytes and endothelial cells depending on the culture medium used. Established hMADS cells populations have a capacity of self-renewal and of adipocytic differentiation that is preserved during a certain number of population doublings, i.e., they are viable in the long term and they can divide without altering the initial cellular characteristics. As a result, such populations can be referred as hMADS cell lines. Advantageously, the hMADS cell populations according to the present invention have a self-renewal capacity and an adipocytic differentiation capacity that are preserved during at least 130, even more advantageously at least 200 population doublings. In the present invention, the conditions enabling the differentiation of the hMADS cell population into a functional human brown adipocytes population have been determined and are described below. A functional human brown adipocytes population could thus be established. This population has the same capacity of self-renewal and of adipocytic differentiation preserved during a certain number of population doublings as the hMADS cell population from which it arises. It is thus viable in the long term and can divide without altering the initial cellular characteristics. As a result, this population can also be referred as a functional brown adipocytes line.

According to the present invention, by "functional" human brown adipocytes population, it is meant a population having a respiratory activity and an uncoupling activity that are significantly higher compared with the respiratory activity and the uncoupling activity of any other cell type, notably compared with those of white adipocytes. Moreover, the significantly higher respiratory activity of the functional human brown adipocytes population is stimulated when this population is exposed to a specific agonist of β-adrenergic receptors such as isoproterenol. The significantly higher respiratory activity and uncoupling activities in the functional human brown adipocytes population, as well as the stimulation of respiratory activity by a specific agonist of β-adrenergic receptors, are due to the expression of the gene coding for UCP1 compared with the absence of the expression of the same gene in human white adipocytes. The uncoupling activity of the UCP1 protein results from the presence of said protein in the inner mitochondrial membrane of human brown adipocytes. Significantly higher respiratory and uncoupling activities by these human brown adipocytes would not be observed if the UCP1 protein was not both localized and functional in the inner mitochondrial membrane. The functionality of human brown adipocytes can be verified in various ways, as described below.

In the present invention, by "respiratory activity" it is meant the capacity of a cell or of a cell population to consume oxygen. This capacity to consume oxygen can be measured as indicated below.

In the present invention, by "uncoupling activity" it is meant the capacity of the UCP1 protein, and consequently the capacity of the cell that contains it, to uncouple its respiratory activity from its ATP production. Indeed, when the cell respires, it produces a proton gradient between the interior and the exterior of the inner mitochondrial membrane. This gradient enables the generation of ATP. However, the UCP1 protein dissipates this proton gradient. This leads to a strong decrease in ATP production and an increase in heat production. Thus, for a given ATP production, a brown adipocyte will consume much more oxygen than a white adipocyte. The measurement of uncoupling activity is indicated below.

In the present invention, expression of a gene by a cell population means that the product resulting from this expression is either the translation product of said gene, namely the protein encoded by the gene, or the transcription product of said gene, namely the mRNA encoding the protein. The expression of a gene is determined by the quantification of either the translation product (the protein coded by the gene), for example by using the immunoblotting technique, or the transcription product (the mRNA coding for the protein), for example by quantitative RT-PCR and/or the Northern blot technique. Quantifying techniques of gene expression products are well known to the person skilled in the art.

The expression of the genes encoding the UCP1, CIDEA, CPT1B, Bcl-2, Bax, PPARα, PGC-1α, PGC-1β and PRDM16 proteins by the functional human brown adipocytes population is quantified and then compared with the expression of these same genes by a human white adipocytes population. This human white adipocytes population advantageously arises from a hMADS cells population as described above. The culture conditions allowing the differentiation of hMADS cells into human white adipocytes are notably described in the international application WO 2004/013 275 published on Feb. 12, 2004, page 17, line 36 to page 18, line 8, or in the Examples section of the present patent application. Advantageously, the human white adipocytes population is obtained after stimulating a hMADS cell population for 1 to 9 days, advantageously for 6 days, with a specific agonist of the PPARγ receptor such as a compound of the thiazolidinediones family, said compound being advantageously selected from rosiglitazone, ciglitazone, pioglitazone, darglitazone and troglitazone.

In the present invention, the expression of a gene by the functional human brown adipocytes population is considered to be higher or lower than the one of the same gene by a human white adipocytes population when a significant difference in this expression is observed. Conversely, a difference is not significant when the expression of a gene by the functional human brown adipocytes population is ±0.20 times identical to the one of the same gene by a human white adipocytes population.

Advantageously, the expression of the gene coding for the UCP1 protein is 10 to 1000 times higher, preferably 20 to 500 times higher than the expression of this same gene by the human white adipocytes population, and/or the expression of the gene encoding the CIDEA protein is 10 to 100 times higher, preferably 20 to 100 times higher than the expression of this same gene by the human white adipocytes population, and/or the expression of the gene encoding the CPT1B protein is 2 to 10 times higher, preferably 4 to 8 times higher than the expression of this same gene by the human white adipocytes population, and/or the expression of the gene encoding the Bcl-2 protein is 1.5 to 4 times higher, preferably 2 to 3 times higher than the expression of this same gene by the human white adipocytes population, and/or the expression of the gene encoding the Bax protein is 0.25 to 2.5 times lower, preferably 0.5 to 2 times lower than the expression of this same gene by the human white adipocytes population, and/or the expression of the genes encoding the PPARα, PGC-1α, PGC-1β and PRDM16 proteins is ±0.20 times identical to the expression of these same genes by the human white adipocytes population.

According to an advantageous embodiment, the expression of the gene encoding UCP1 is increased after stimulation by a β-adrenergic receptor agonist, advantageously after stimulation by a β3-adrenergic receptor agonist, advantageously for a duration comprised between 1 and 24 hours, advantageously 6 hours. Advantageously, the expression of the gene encoding UCP1 is 1.5 to 4 times higher compared with the one obtained in the absence of stimulation by a β-adrenergic receptor agonist.

Any specific β-adrenergic receptor agonist can be used. Examples of such agonists are notably cited in table 1 of Carpene, C. Methods Mol Biol 2001. 155, 129-140. One can notably cite, without limiting oneself, the compounds noradrenalin and adrenalin, the compound T0509 (β1), the compounds salbutamol and procaterol (β2), the compound BRL37314 (β3), dobutamine, terbutaline, isoproterenol, which is a specific agonist of the three β1-, β2- and β3-adrenergic receptors, the compound CGP12177A, which is a partial agonist of the β3-adrenergic receptor, and the compound CL316243, which is a specific agonist of the β3-adrenergic receptor. Advantageously, the specific β3-adrenergic receptor agonist is selected from dobutamine, terbutaline, isoproterenol, noradrenalin, adrenalin, the compound CGP12177A, which is a partial agonist of the β-adrenergic receptor, and the compound CL316243, which is a specific agonist of the β3-adrenergic receptor. Still more advantageously, the specific β-adrenergic receptor agonist is selected from the compounds noradrenalin, adrenalin, isoproterenol and CL316243. The compounds dobutamine, terbutaline isoprenaline and CL316243 can notably be obtained from Sigma Chemical Company (St. Louis, Mo., USA). The compound CGP12177A can be obtained from Research Biochemical (Natick, Mass., USA).

Also advantageously, the concentration of specific β-adrenergic receptor agonist is comprised between 1 nM and 1000 nM, advantageously between 1 nM and 500 nM, even more advantageously between 1 and 100 nM.

The invention also relates to the use of a specific β3-adrenergic receptor agonist to increase the expression of the gene encoding the UCP1 protein in a human brown adipocytes population such as the population according to the present invention. Advantageously, the invention relates to the use of a specific β3-adrenergic receptor agonist to increase the UCP1 protein uncoupling activity in a human brown adipocytes population such as the population according to the present invention. Preferably, the agonist is the compound CL316243, and is preferably used at a concentration comprised between 1 nM and 1000 nM, advantageously between 1 nM and 500 nM, even more advantageously between 1 nM and 100 nM.

According to a second aspect, the present invention relates to a method for differentiating a population of human multipotent adipose-derived stem cells (hMADS cells) into a functional human brown adipocytes population such as defined in the present invention, comprising the stimulation of the aforesaid hMADS cells by a specific PPARγ receptor agonist, this stimulation being carried out:
 either for a duration period comprised between 10 and 30 days, advantageously between 13 and 20 days, even more advantageously between 15 and 16 days, or
 (i) for a first differentiation period of hMADS cells into white adipocytes of a duration comprised between 2 and 9 days, advantageously between 3 and 7 days, even more advantageously of 6 days, (ii) said first period being followed by a second period of a duration comprised between 2 and 10 days, advantageously between 4 and 7 days, even more advantageously 5 days, during which stimulation is stopped, (iii) said second period being followed by a third stimulation period of a duration comprised between 1 and 10 days, advantageously between 1 and 6 days, even more advantageously of 2 days.

Any specific PPARγ receptor agonist can be used in the context of the present invention. One can cite, without limiting oneself, a thiazolidinedione such as rosiglitazone, ciglitazone, pioglitazone, darglitazone, troglitazone or the compound NC-2100. One can also cite the compound 526948, compounds derived from N-(2-Benzoylphenyl)-L-tyrosine, FMOC derivatives, 1,3-dicarbonyl compounds comprising 2(3H)benzazolonic heterocycles, compounds of the family of sulfonylureas, compounds of the family of 2-benzoylaminobenzoic acids substituted in position 5, the compound halofenate, derivatives of the family of indene-N-oxides, type-1 angiotensin receptor antagonists such as telmisartan, irbesartan and losartan. Advantageously, the specific PPARγ receptor agonist is a thiazolidinedione, said thiazolidinedione being even more advantageously selected from the group comprised of rosiglitazone, ciglitazone, pioglitazone, darglitazone and troglitazone. The ciglitazone and troglitazone compounds can notably be obtained from Cayman Chemical (Ann Arbor, Mich., USA). The pioglitazone and rosiglitazone compounds can be obtained from Sigma Chemical Co. (St Louis, Mo., USA). Darglitazone can be obtained from Medicinal Chemistry, AstraZeneca R&D (Molndal, Sweden).

Advantageously, when the specific PPARγ receptor agonist is rosiglitazone, the concentration in rosiglitazone is comprised between 5 nM and 1,000 nM, advantageously between 10 nM and 500 nM, even more advantageously between 20 and 100 nM. Also advantageously, when the specific PPARγ receptor agonist is pioglitazone, the concentration in pioglitazone is comprised between 0.2 µM and 10 µM, advantageously between 0.4 µM and 5 µM, even more advantageously between 0.8 µM and 2 µM. Also advantageously, when the specific PPARγ receptor agonist is ciglitazone, the concentration in ciglitazone is comprised between 0.5 µM and 20 µM, advantageously between 1 µM and 10 µM, even more advantageously between 2 µM and 4 µM. Also advantageously, when the specific PPARγ receptor agonist is darglitazone, the concentration in darglitazone is comprised between 0.2 µM and 20 µM, advantageously between 0.5 µM and 10 µM, even more advantageously between 1 µM and 5 µM. Also advantageously, when the specific PPARγ receptor agonist is troglitazone, the concentration in troglitazone is comprised between 0.2 µM and 10 µM, advantageously between 0.5 µM and 5 µM, even more advantageously between 1 µM and 4 µM.

The general culture conditions used for the multiplication and differentiation of the hMADS cell population are known to the person skilled in the art and are notably described in application WO 2004/013 275, or in the Examples section of the present patent application. The culture medium used for the differentiation of the hMADS cell population is regularly changed, preferably every 2 days, before using the cells. This medium does not advantageously contain serum such as newborn calf serum and is chemically defined.

The functionality of the human brown adipocytes population according to the invention can moreover be verified by stimulating its respiratory activity using a specific β-adrenergic receptor agonist such as isoproterenol. Thus, according to a preferred embodiment, the method for differentiating the hMADS cell population into a human brown adipocytes population according to the present invention, further comprises the verification of the functionality of the obtained human brown adipocytes population, said verification comprising the following successive steps:

stimulating the respiratory activity of said human brown adipocytes population by a specific β-adrenergic receptor agonist, quantificating the expression of the gene encoding UCP1 and/or the oxygen consumption, and verifying that said population is functional when the expression of the gene encoding UCP1 and/or the oxygen consumption is increased compared with the one obtained in the absence of stimulation by the specific β-adrenergic receptor agonist.

When the population is functional, a strong stimulation of respiratory activity is observed, such as an increase of at least 20%, preferably at least 40% compared with the absence of stimulation by the specific β-adrenergic receptor agonist. In comparison, no stimulation is observed when white adipocytes are exposed to a specific β-adrenergic receptor agonist.

Preferably, the expression of the gene encoding UCP1 is 1.5 to 4 times higher compared with the one obtained in the absence of stimulation by a β-adrenergic receptor agonist.

Advantageously, the specific β-adrenergic receptor agonist is selected from isoprenaline, noradrenalin, adrenalin, dobutamine, terbutaline and the compound CL316243, advantageously isoproterenol.

Also advantageously, the concentration in specific β-adrenergic receptor agonist is comprised between 1 nM and 1,000 nM, advantageously between 1 nM and 500 nM, even more advantageously between 1 nM and 100 nM.

The functionality of the human brown adipocytes population can be verified, for example, by quantifying oxygen consumption using a respirometer. Such a technique is well known to the person skilled in the art.

The functionality of the human brown adipocytes population can also be verified by quantifying the uncoupling activity of said population. This quantification of uncoupling activity can be carried out using an uncoupling agent such as carbonyl cyanide 3-chlorophenylhydrazone (CCCP). Such a technique is well known to the person skilled in the art.

According to a third aspect, the present invention relates to a method for converting a human white adipocytes population into a functional human brown adipocytes population such as defined in the present invention, comprising the stimulation of said human white adipocytes population with a specific PPARγ agonist for a duration comprised between 1 and 10 days, advantageously between 1 and 6 days, even more advantageously of 2 days.

The human white adipocytes population is such as described above. The culture medium used for the converting the human white adipocytes population is the same as the one used for differentiating hMADS cells. Similarly, this medium is regularly changed, preferably every 2 days, before using the cells.

The specific PPARγ receptor agonist is such as defined above.

Advantageously, the specific PPARγ receptor agonist is a thiazolidinedione, said thiazolidinedione being advantageously selected from the group comprised of rosiglitazone, ciglitazone, pioglitazone, darglitazone and troglitazone.

Advantageously, when the specific PPARγ receptor agonist is rosiglitazone, the concentration in rosiglitazone is comprised between 5 nM and 1,000 nM, advantageously between 10 nM and 500 nM, even more advantageously between 20 nM and 100 nM. Also advantageously, when the specific PPARγ receptor agonist is pioglitazone, the concentration in pioglitazone is comprised between 0.2 μM and 10 μM, advantageously between 0.4 μM and 5 μM, even more advantageously between 0.8 μM and 2 μM. Also advantageously, when the specific PPARγ receptor agonist is ciglitazone, the concentration in ciglitazone is comprised between 0.5 μM and 20 μM, advantageously between 1 μM and 10 μM, even more advantageously between 2 μM and 4 μM. Also advantageously, when the specific PPARγ receptor agonist is darglitazone, the concentration in darglitazone is comprised between 0.2 μM and 20 μM, advantageously between 0.5 μM and 10 μM, even more advantageously between 1 μM and 5 μM. Also advantageously, when the specific PPARγ receptor agonist is troglitazone, the concentration in troglitazone is comprised between 0.2 μM and 10 μM, advantageously between 0.5 μM and 5 μM, even more advantageously between 1 μM and 4 μM.

In a preferred embodiment, the method for converting according to the present invention comprises also the verification of the functionality of the human brown adipocytes population obtained after converting the human white adipocytes population, said verification comprising the following successive steps:
  stimulating the respiratory activity of said human brown adipocytes population with a specific β-adrenergic receptor agonist,
  quantifying the expression of the gene encoding UCP1 and/or the oxygen consumption, and
  verifying that said population is functional when the expression of the gene encoding and/or the oxygen consumption is increased compared with the one obtained in the absence of stimulation by the specific β-adrenergic receptor agonist.

Preferably, the expression of the gene encoding UCP1 is 1.5 to 4 times higher compared with the one obtained in the absence of stimulation by a β-adrenergic receptor agonist.

Advantageously, the specific β-adrenergic receptor agonist is selected from isoprenaline, noradrenalin, adrenalin, dobutamine, terbutaline and the compound CL316243, advantageously isoproterenol.

Also advantageously, the concentration in specific β-adrenergic receptor agonist is comprised between 1 nM and 1,000 nM, advantageously between 1 nM and 500 nM, even more advantageously between 1 and 100 nM.

The present invention also relates to the human brown adipocytes population obtained by the method for differentiating or the method for converting such as defined in the present invention.

According to another aspect, the present invention relates to the use of a functional human brown adipocytes population according to the present invention as a model to identify a molecule or a combination of molecules capable of modulating the body weight in an individual, advantageously to identify a molecule or a combination of molecules capable of treating excess weight and/or obesity in an individual. Advantageously, the individual is a human being.

Advantageously, the present invention relates to a method for identifying a molecule or combination of molecules capable of acting on the respiratory activity and/or the uncoupling activity of a brown adipocytes population and/or of modulating the body weight in an individual, comprising the following successive steps:
  placing the functional human brown adipocytes population according to the present invention in the presence of said molecule or combination of molecules,
  quantifying the expression of the gene encoding UCP1 and/or the oxygen consumption and/or the uncoupling activity of said human brown adipocytes population, and
  identifying said molecule or combination of molecules as being capable of acting on the respiratory activity and/or the uncoupling activity of a brown adipocytes population and/or of modulating the body weight in an individual when the expression of the gene encoding UCP1 and/or the oxygen consumption and/or uncoupling activity is significantly different from the one obtained in the absence of said molecule.

According to an advantageous embodiment, when the expression of the gene encoding UCP1 and/or the oxygen consumption and/or uncoupling activity are higher than the one obtained in the absence of the molecule or combination of molecules, said molecule or combination of molecules is capable of increasing the respiratory activity and/or the uncoupling activity of a brown adipocytes population and/or of treating excess weight and/or obesity in an individual.

Also advantageously, the present invention relates to a method for identifying a molecule or combination of molecules capable of promoting the formation of human brown adipocytes and/or of treating excess weight and/or obesity in an individual, comprising the following successive steps:
  placing a hMADS cells population in the presence of said molecule or combination of molecules,
  identifying said molecule or combination of molecules as being capable of promoting the formation of human brown adipocytes and/or of treating excess weight and/or obesity in an individual when the population of hMADS cells expresses the phenotype of a functional human brown adipocytes population according to the present invention.

According to the present invention, by "phenotype of a functional human brown adipocytes population" it is meant that said population simultaneously expresses the genes encoding the UCP1, CIDEA, CPT1B, Bcl-2, Bax, PPARα, PGC-1α, PGC-1β and PRDM16 proteins as described above. Also, said population has an increased respiratory activity, which can be stimulated with a specific β-adrenergic receptor agonist such as isoproterenol. This phenotype can be determined as described above (immunoblotting, Northern blot, quantitative RT-PCR, respirometer, etc.).

Also advantageously, the present invention relates to a method for identifying a molecule or combination of molecules capable of promoting the formation of human brown adipocytes and/or of treating excess weight and/or obesity in an individual, comprising the following successive steps:
  placing a human white adipocytes population in the presence of said molecule or combination of molecules,
  identifying said molecule or combination of molecules as being capable of promoting the formation of human brown adipocytes and/or of treating excess weight and/or obesity in an individual when the human white adipocytes population expresses the phenotype of a human brown adipocytes population according to the present invention.

The human white adipocytes population is such as defined above.

The examples and figures which follow illustrate the present invention without limiting its scope in any way.

BRIEF DESCRIPTION OF THE SEVERAL VIEWS OF THE DRAWINGS

Not Applicable

DETAILED DESCRIPTION OF THE SEVERAL VIEWS OF THE DRAWINGS

Figures

Figure 1:
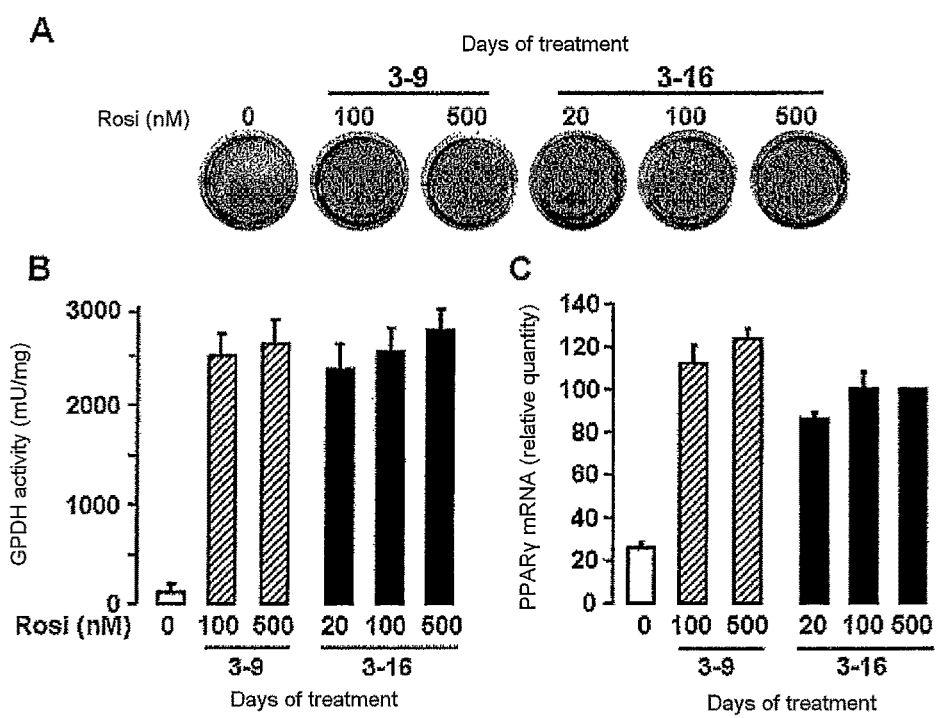

FIG. 1: Effect of rosiglitazone on adipocytic differentiation of hMADS-2 cells

Adipocytic differentiation of hMADS-2 cells was carried out according to the protocol described in the "Materials and Methods" section. Rosiglitazone was added at the concentrations and on the days indicated. The following were performed on day 16: A) the cells were fixed and then stained with Oil Red O, B) GPDH activity was measured, and C) PPARγ mRNA levels were determined by quantitative RT-PCR. The results represent the mean±SD of 3 independent experiments carried out with various series of cells; 100% corresponds (C) to the value obtained on day 16 in the presence of 500 nM rosiglitazone.

Figure 2:
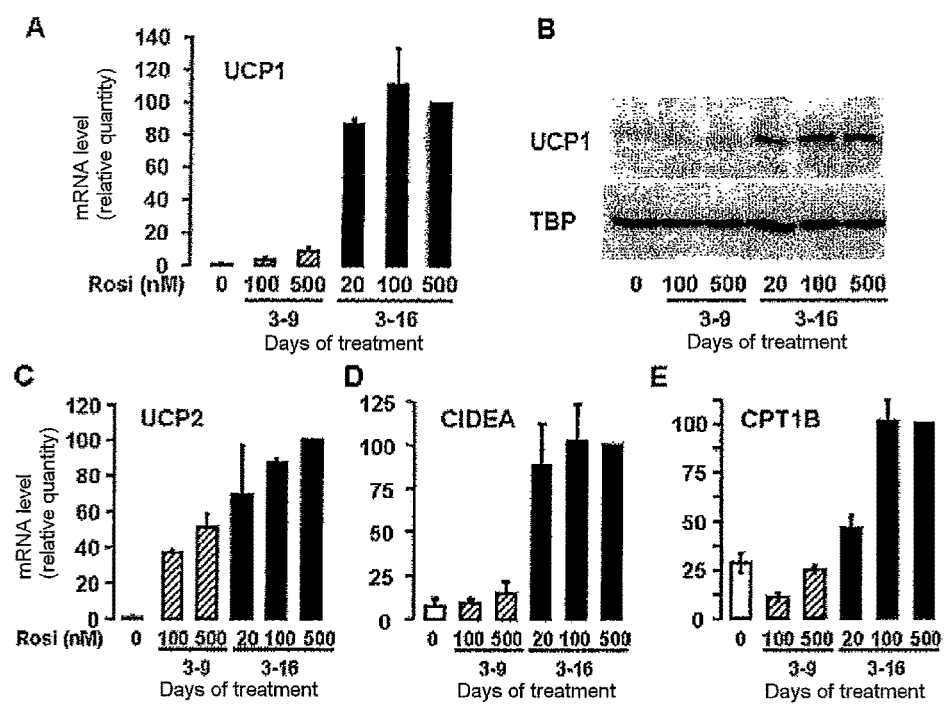

FIG. 2: Effect of long-term exposure of hMADS-2 cells to rosiglitazone on expression of brown adipocytes markers Differentiation of hMADS-2 cells was carried out as described in FIG. 1. On day 16, levels of UCP1 (A), UCP2 (C), CIDEA (D) and CPT1B (E) mRNA were determined by quantitative RT-PCR. The results represent the mean±SD of 3 independent experiments carried out with various series of cells; they are expressed by taking as 100% the value obtained in the presence of 500 nM rosiglitazone. Levels of the UCP1 protein (B) were determined by immunoblotting on 2 different series of cells using TBP as endogenous internal standard.

Figure 3:
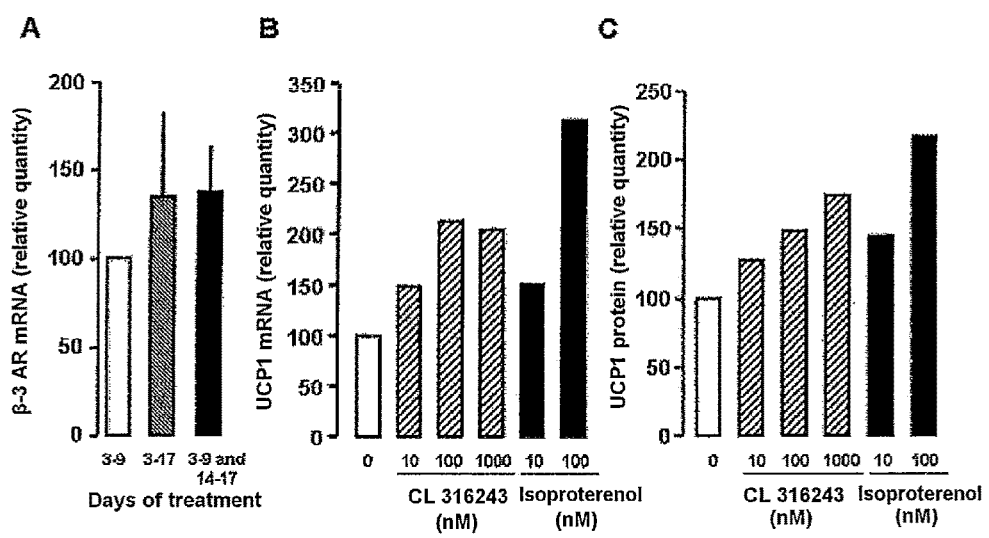

FIG. 3: Expression of β3-adrenergic receptors and stimulation of expression of UCP1 in response to β-adrenergic agonists A) adipocytic differentiation of hMADS-2 cells was carried out in the presence of 100 nM rosiglitazone on the days indicated and mRNA levels were determined on day 17 by quantitative RT-PCR. (B, C) differentiation was obtained in the presence of 100 nM rosiglitazone between days 3 and 16, in the absence or the presence during the 6 last hours of β-adrenergic agonists at the indicated concentrations. The results represent the mean±SD of 3 (A) and 2 (B) independent experiments carried out with various series of cells; they are expressed by taking as 100% the values obtained either during treatment between days 3 and 9 (A) or in the absence of β-adrenergic agonists (B, C).

Figure 4:
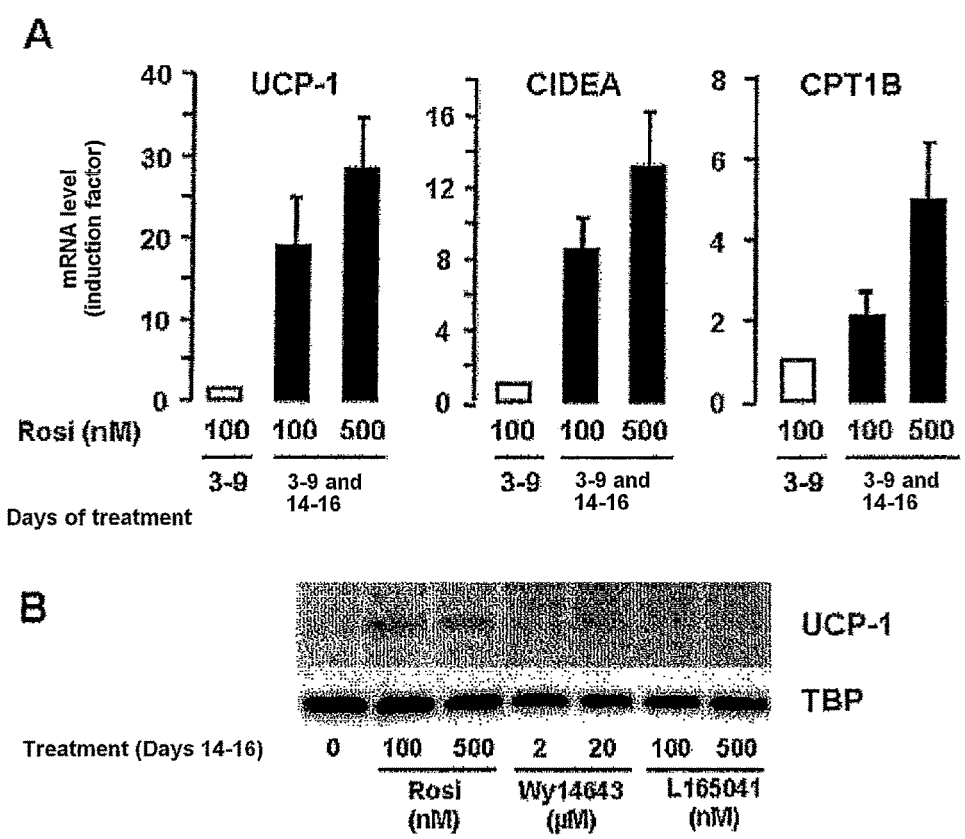

FIG. 4: The induction of a brown phenotype from white adipocytes is dependent upon PPARγ activation Initially hMADS-2 cells were differentiated into white adipocytes with 100 nM rosiglitazone present between days 3 and 9. Once eliminated, the ligand is added or not added on day 14 and during the following days at the indicated UCP1, CIDEA and CPT1B concentrations. On day 16, mRNA levels of UCP1, CIDEA and CPT1B were determined by quantitative RT-PCR (A) and the quantity of the UCP1 protein was determined by immunoblotting after exposure between days 14 and 16 with specific PPAR ligands (B).

The results are expressed as stimulation factor by taking as 1 the values obtained on day 16 after exposure to 100 nM rosiglitazone between days 3 and 9; the values represent the mean±SD of 2 independent experiments carried out with various series of cells.

Figure 5:
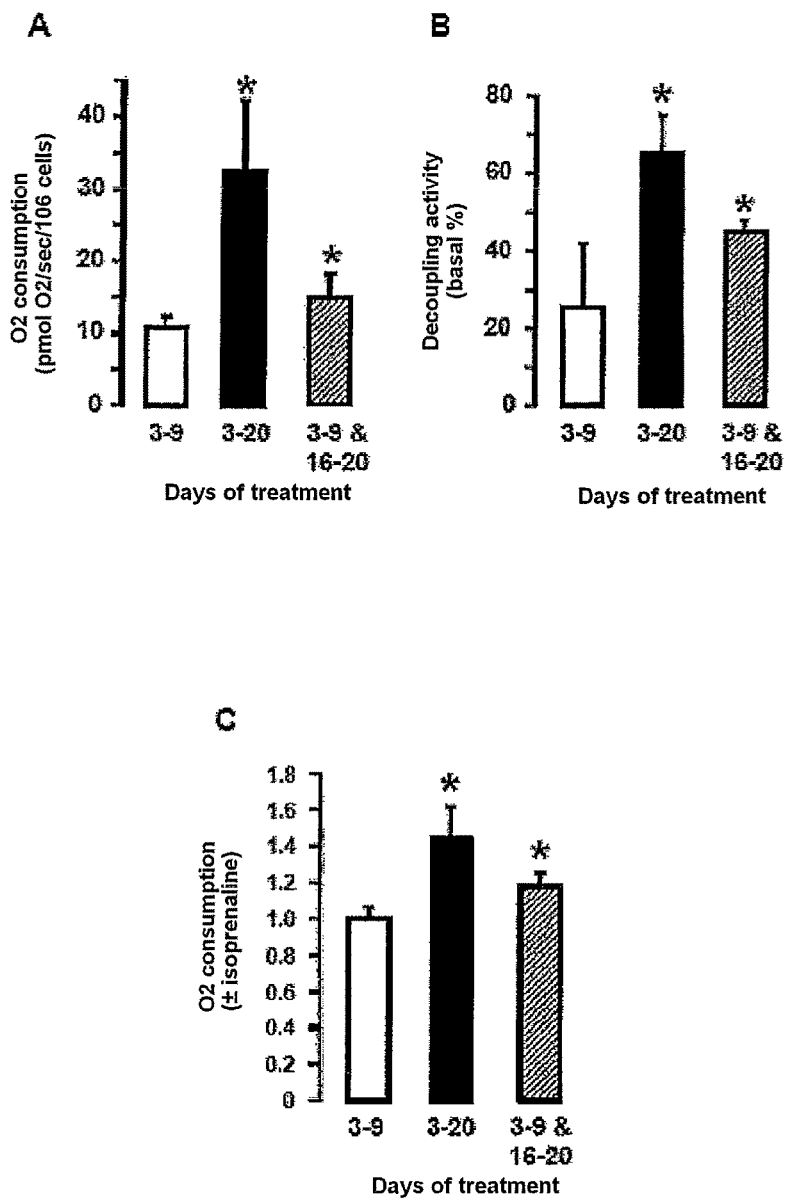

FIG. 5: Effect of long-term treatment with rosiglitazone on respiratory and uncoupling activities of white and brown adipocytes hMADS-2 cells were induced to differentiate in the presence of 100 nM rosiglitazone either during days 3 and 9 to obtain white adipocytes, or during days 3 and 20 to obtain brown adipocytes, or finally during days 3-9 followed by days 16-20. On day 20, oxygen consumption (A), decoupling of oxidative phosphorylation (B) and stimulation of oxygen consumption by isoprenaline (C) were measured according to the protocol described in "Materials and Methods". The results represent the mean±SD of 4 independent experiments carried out with various series of cells. *P<0.05 by comparison with the cells treated between days 3 and 9 in the presence of 100 nM rosiglitazone.

Figure 6:
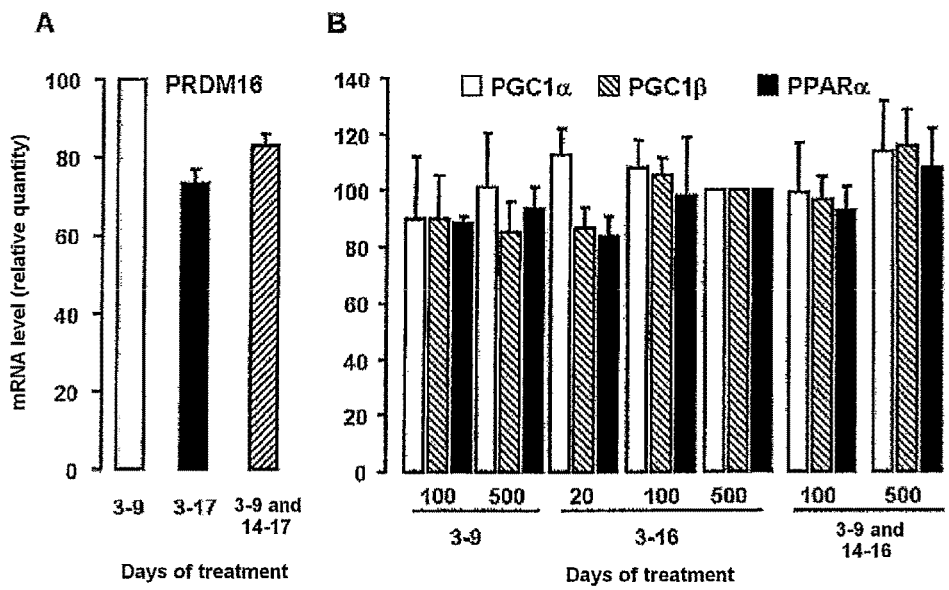

FIG. 6: Gene expression of transcription factors and co-factors as a function of the acquisition of a white or brown phenotype Adipocytic differentiation of hMADS-2 cells was carried out in the presence of either rosiglitazone at 100 nM (A) or at the indicated concentrations (B). Levels of PRDM16, PGC-1α, PGC-1β and PPARα mRNA were determined by quantitative RT-PCR on day 16 (A) and day 17 (B). The results represent the mean±SD of 3 independent experiments carried out with various series of cells; they are expressed by taking as 100% the values obtained in the presence of 100 nM rosiglitazone (A) or 500 nM rosiglitazone (B).

Figure 7:
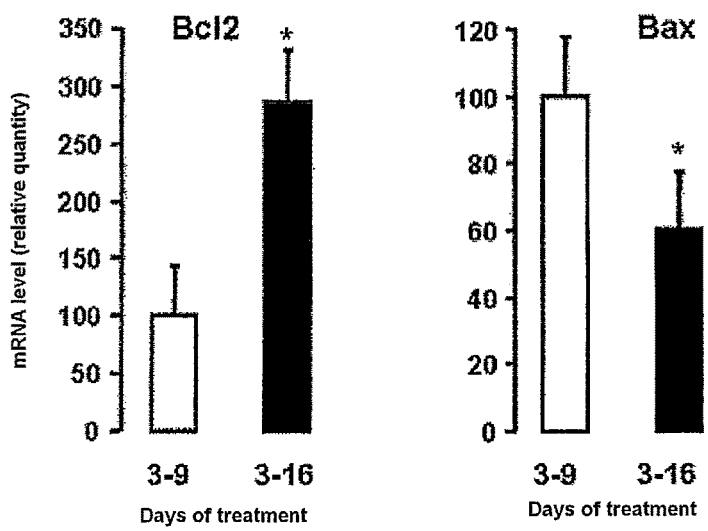

FIG. 7: Expression of genes associated with apoptosis as a function of the acquisition of a white or brown phenotype Adipocytic differentiation of hMADS-2 cells was carried out in the presence of 100 nM rosiglitazone. On day 16, Bcl-2 and Bax mRNA levels were determined by quantitative RT-PCR. The results represent the mean±SD of 3 independent experiments carried out with various series of cells; they are expressed by taking as 100% the values obtained during treatment with rosiglitazone between days 3 and 9. *P0.05.

Figure 8:
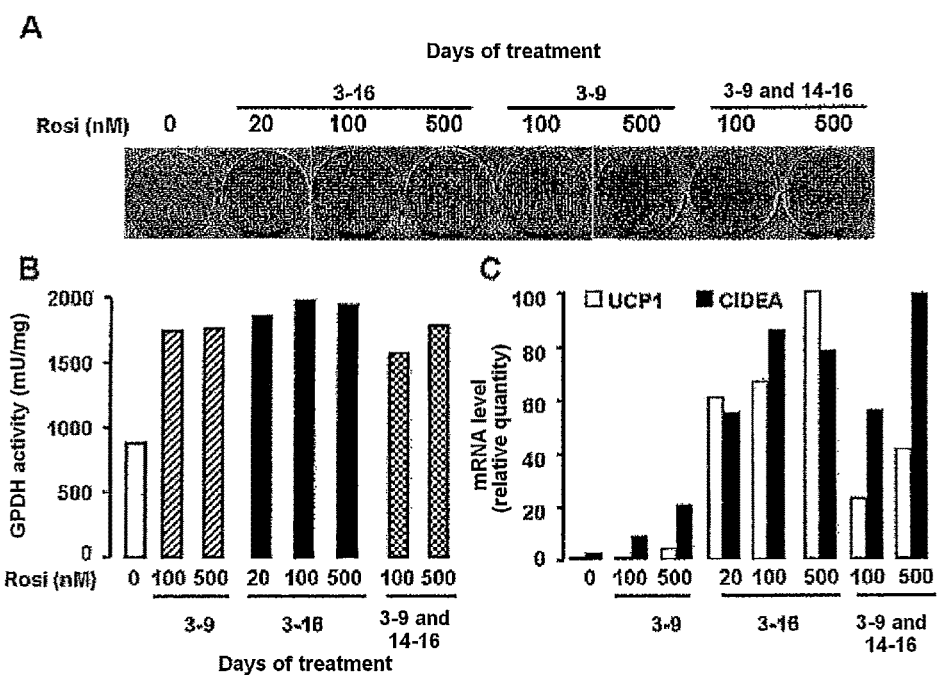

FIG. 8: Effect of rosiglitazone on adipocytic differentiation of hMADS-1 cells hMADS-1 cells were differentiated according to the protocol described in FIG. 1. Exposure to rosiglitazone was carried out at the concentrations and on the days indicated. On day 16, the cells were fixed and stained with Oil Red 0 (A), GPDH activity was determined (B) as well as levels of UCP1 and CIDEA mRNA by quantitative RT-PCR (C). The results represent the mean±SD of 2 independent experiments carried out with various series of cells and are expressed (C) by taking as 100% the value obtained in the presence of 100 nM rosiglitazone on day 16.

DETAILED DESCRIPTION OF THE INVENTION

EXAMPLES

Abbreviations: hMADS cells ("human multipotent adipose-derived stem cells"); WAT ("white adipose tissue"); BAT ("brown adipose tissue"); PPAR ("peroxisome proliferator-activated receptor"); PPRE ("peroxisome proliferator-responsive element"); UCP1 ("uncoupling protein 1"); UCP2 ("uncoupling protein 2"); PGC-1α(β) ("PPARγ coactivator α(β)"); CtBP-1 ("C-terminal-binding protein-1"); AR ("adrenergic receptor"); CIDEA ("cell death-inducing DFF45-like effector A"); NAIP ("neuronal apoptosis inhibitory protein"); CTP-1B ("carnitine palmitoyltransferase-1B"); PKA ("protein kinase A"); T3 ("3,5,3'-tri-iodothyronine"); TBP ("TATA-box binding protein"); PRDM16 ("PR-domain zinc finger protein 16"); Bax ("Bcl-2-associated X protein"); Bcl-2 ("B-cell CLL/lymphoma-2").

I. Materials and Methods

Cell culture: Preparation and characterization of hMADS cell multipotence and self-renewal have been described (Rodriguez, A. M., et al., Biochem Biophys Res Commun, 2004. 315(2): p. 255-63; Rodriguez, A. M., et al., J Exp Med, 2005. 201(9): p. 1397-405; Zaragosi, L. E. et al., Stem Cells, 2006. 24(11): p. 2412-9; Elabd, C, et al., Biochem Biophys Res Commun, 2007. 361(2): p. 342-8). Cells of the hMADS-2 line were established from adipose tissue from the pubic area of a donor aged 5; they were used between passages 16 and 35 (35 to 100 doublings of the cell population). The cells were cultured at a density of 4,500 cells/cm$^2$ in DMEM (Dulbecco's Modified Eagle Medium) enriched with 10% fetal calf serum, 2.5 ng/ml hFGF$_2$, 60 μg/ml penicillin and 50 μg/ml streptomycin. After a change of medium every 2 days, when the cells become confluent, hFGF$_2$ is eliminated and the cells induced to differentiate 2 days later, defining day 0 of differentiation. The adipocyte differentiation medium consists of DMEM/H12 (1:1, v/v) enriched with 10 μg/ml transferrin, 0.85 μM insulin, 0.2 nM T$_3$, 1 μM dexamethasone (DEX) and 500 μM isobutylmethylxanthine (IBMX). Three days later, the medium is changed (DEX and IBMX omitted) and rosiglitazone added at the indicated concentrations and days. The medium is then changed every 2 days before using the cells. The determination of glycerol-3 phosphate dehydrogenase (GPDH) activity and lipid staining with Oil Red 0 have been previously described (Negrel, R. et al., Proc Natl Acad Sci USA, 1978. 75(12): p. 6054-8; Bezy, O., et al., J Biol Chem, 2005. 280(12): p. 11432-8).

RNA purification and analysis: RNA extraction, the use of reverse transcriptase and determination of mRNA levels by real-time quantitative RT-PCR have been described (Zaragosi, L. E et al., Stem Cells, 2006. 24(11): p. 2412-9; Elabd, C, et al., Biochem Biophys Res Commun, 2007. 361(2): p. 342-8; Bezy, O., et al., J Biol Chem, 2005. 280(12): p. 11432-8). Expression of the genes of interest was normalized compared with the one of the TBP gene and was quantified using the ΔCt comparative method. The sequences of oligonucleotide primers, obtained using the Primer Express Software (Perkin Elmer Life Sciences), are described in Table 1 below.

TABLE 1

Oligonucleotide primers sequence for gene expression analysis

| | Sense primer | Antisense primer | Accession number |
|---|---|---|---|
| FABP4 | TGTGCAGAAATGGGATGGAAA SEQ ID NO. 1 | CAACGTCCCTTGGCTTATGCT SEQ ID NO. 2 | NM_001442 |
| UCP-1 | GTGTGCCCAACTGTGCAATG SEQ ID NO. 3 | CCAGGATCCAAGTCGCAAGA SEQ ID NO. 4 | NM_021833 |
| UCP-2 | GGCCTCACCGTGAGACCTTAC SEQ ID NO. 5 | TGGCCTTGAACCCAACCAT SEQ ID NO. 6 | NM_003355 |
| PPARγ | AGCCTCATGAAGAGCCTTCCA SEQ ID NO. 7 | TCCGGAAGAAACCCTTGCA SEQ ID NO. 8 | NM_005037 |
| PPARα | GGCGAACGATTCGACTCAAG SEQ ID NO. 9 | TCCAAAACGAATCGCGTTGT SEQ ID NO. 10 | NM_032644 |
| PGC-1α | CTGTGTCACCACCCAAATCCTTAT SEQ ID NO. 11 | TGTGTCGAGAAAAGGACCTTGA SEQ ID NO. 12 | NM_013261 |
| PGC-1β | GCGAGAAGTACGGCTTCATCAC SEQ ID NO. 13 | CAGCGCCCTTTGTCAAAGAG SEQ ID NO. 14 | NM_133263 |
| PRDM16 | GAAACTTTATTGCCAATAGTGAGATGA SEQ ID NO. 15 | CCGTCCACGATCTGCATGT SEQ ID NO. 16 | NM_022114 |
| β3-AR | GCCTTCGCCTCCAACATG SEQ ID NO. 17 | AGCATCACGAGAAGAGGAAGGT SEQ ID NO. 18 | NM_000025 |
| CIDEA | GGCAGGTTCACGTGTGGATA SEQ ID NO. 19 | GAAACACAGTGTTTGGCTAAGA SEQ ID NO. 20 | NM_001279 |
| CPT1B | AAACAGTGCCAGGCGGTC SEQ ID NO. 21 | CGTCTGCCAACGCCTTG SEQ ID NO. 22 | NM_152246 |
| Bax | TGCCTCAGGATGCGTCCACCAA SEQ ID NO. 23 | CGGCAATCATCCTCTGCAGCTCCAT SEQ ID NO. 24 | NM_004324 |
| Bcl-2 | GCCCCCGTTGCTTTTCC SEQ ID NO. 25 | CCGGTTATCGTACCCTGTTCTC SEQ ID NO. 26 | NM_000657 |
| TBP | CACGAACCACGGCACTGATT SEQ ID NO. 27 | TTTTCTTGCTGCCAGTCTGGAC SEQ ID NO. 28 | NM_003194 |

Immunoblot analysis: Total cellular lysates are analyzed by immunoblot as previously described (Bezy, O., et al., J Biol Chem, 2005. 280(12): p. 11432-8). The primary antibodies obtained from the rabbit, anti-human UCP1 and anti-TBP, are products from Santa Cruz Biotechnology (Santa Cruz, Calif., USA) and the secondary antibodies (conjugated with horseradish peroxidase) are products from Promega (Charbonnières, France). The "Enhanced Chemiluminescence" system (Millipore, Saint-Quentin-Yvelines, France) was used for detection.

Determination of oxygen consumption: Oxygen consumption was measured using two-chamber injection respirometer equipped with a Peltier thermostat, Clark electrodes and integrated magnetic stirrers (Oroboros, Innsbruck, Austria). Measurements were made at 37° C. with constant stirring in a volume of 2 ml of DMEM/F12 medium (1:1, v/v) containing 10% fetal calf serum. Before each measurement, the medium present in the chambers was equilibrated with air for 30 min, and then the freshly-trypsinized cells were transferred to this medium. After having reached a stationary respiratory state, ATP synthase was inhibited using oligomycin (0.25-0.5 mg/l) and the respiratory activity of the cells titrated in the presence of the uncoupling agent carbonyl cyanide 3-chlorophenylhydrazone (CCCP) at optimal concentrations of 1-2 μM. The respiratory chain was blocked with 1 μg/ml antimycin A. Oxygen consumption was calculated using the DataGraph software (Oroboros Software). Basal respiratory activity corresponds to oxygen consumption sensitive to antimycin A. Respiratory activity was stimulated in the presence of 1 μM isoprenaline added extemporaneously in the injection chamber, with measurements made as described above.

Statistical analysis: The data are expressed as mean±SD and are analyzed by the Student's t-test. Differences are considered significant for $p<0.05$.

II. Results

UCP1 and Brown Adipocyte Markers are Expressed During the hMADS Cells Differentiation As previously described (Rodriguez, A. M., et al., Biochem Biophys Res Commun, 2004. 315(2): p. 255-63), the PPARγ activation is necessary for adipocytic differentiation of hMADS-2 cells (FIG. 1A). The cells treatment for 6 days with increasing concentrations of rosiglitazone, between days 3 and 9, leads to lipid accumulation and to the expression of GPDH and PPARγ genes. An additional treatment of one week does not change the expression of GPDH and PPARγ genes. On day 16, 20 nM rosiglitazone is sufficient to induce a maximum response, which is consistent with the PPARγ affinity for this ligand (FIG. 1A-C). The totality of the results underscores that a 6-day exposure of hMADS-2 cells to rosiglitazone enables the maximum expression of key white adipocytes markers. On the other hand, such an exposure between days 3 and 9 leads only to a very weak expression of mRNA and the UCP1 protein. However, a 20 nM exposure between days 3 and 16 leads to their strong expression (FIG. 2A, B). Contrary to UCP1, a strong expression of UCP2 mRNA is still observed on day 9; it is increased by a longer exposure (FIG. 2C) and the UCP2 protein is then detected (B. Miroux and C. Ricquier, personal communication). These results suggest that the duration of treatment with rosiglitazone modulates the expression of the UCP1 gene. Similarly, expression of the CIDEA gene, reported as closely associated with that of UCP1, is increased (FIG. 2D) (Zhou, Z., et al., Nat Genet, 2003. 35(1): p. 49-56). Compared with white adipocytes, brown adipocytes have very high mitochondriogenesis (Wilson-Fritch, L., et al., J Clin Invest, 2004. 114(9): p. 1281-9). Indeed, the levels of mRNA coding for mitochondrial carnitine palmitoyltransferase (CPT1B) are strongly increased when hMADS-2 cells switch from the white phenotype to the brown phenotype (FIG. 2E). Unexpectedly, levels of PPARα, PGC-1α, PGC-1β and PRDM16 are similar in adipocytes expressing the white or brown phenotypes (FIG. 6). It is known that rodent brown adipocytes are more susceptible to apoptosis than white adipocytes in vitro and in vivo. These adipocytes express both the anti-apoptotic Bcl-2 protein and the pro-apoptotic Bax protein (Briscini et al., FEBS Lett 1998. 431, 80-84; Lindquist and Rehnmark, J Biol Chem 1998. 273, 30147-30156; Nisoli et al., Cell Death Differ 2006. 13, 2154-2156). Contrary to rodents, human white adipocytes have a high susceptibility to apoptosis which appears to be related to the weak expression of the anti-apoptotic genes Bcl-2 and NAIP (Papineau et al., Metabolism 2003. 52, 987-992). Unexpectedly, the switch of hMADS cells from the white phenotype to the brown phenotype is accompanied by an increase in the expression of the anti-apoptotic gene Bcl-2 and a decrease in the expression of the pro-apoptotic Bax gene, with the ratio of Bcl-2 to Bax passing from 1 to 3.7 (FIG. 7), which implies, depending on the species, a different expression pattern of genes associated with apoptosis. Insofar as UCP1 (FIG. 2), β3-adrenergic receptor (FIG. 3A) and β2-AR receptor (result not shown) are expressed when hMADS-2 cells are exposed to rosiglitazone between days 3 and 16, the functional response to β-agonists was analyzed. As FIGS. 3B and 3C indicate, the expression of UCP1 mRNA and UCP1 protein are significantly increased after a stimulation for 6 h with isoproterenol, a pan-agonist for β receptors, and by the compound CL316243, a selective β3 agonist, at concentrations of 10-100 nM. In short, a prolonged chronic activation of PPARγ leads to the expression of UCP1 and to the acquisition of a functional response to β agonists.

Regulation of UCP1 Expression Occurs in hMADS Cells Previously Differentiated into White Adipocytes With the previous experiments, it is not possible to know if a long-term treatment of hMADS cells is necessary for the acquisition of a brown phenotype, or if a brief exposure to rosiglitazone of hMADS cells already differentiated into white adipocytes enables their transdifferentiation. For this purpose, hMADS-2 cells were exposed beforehand to rosiglitazone between days 3 and 9, the ligand eliminated and then added between days 14 and 16. The results show that this 2-day treatment of white adipocytes is sufficient to stimulate the expression of UCP1, CIDEA and CPT1B genes (FIG. 4A). This effect is specific to PPARγ, the activation of PPARβ/δ and PPARα by the specific ligands Wy14643 and L165041, respectively, not inducing the expression of the UCP1 protein. The replacement of rosiglitazone by polyunsaturated fatty acids as activators/ligands of PPARs (arachidonic, eicosapentaenoic and docosahexaenoic acids present at 10 μM) appears to have no effect on the UCP1 gene expression (results not shown). All these observations show that a specific activation of PPARγ for a brief period is sufficient for the white adipocytes to acquire a brown adipocyte phenotype. The rosiglitazone effects on UCP1 expression are not restricted to hMADS-2 cells; they are also observed with hMADS-1 and hMADS-cells (Rodriguez, A. M., et al., J Exp Med, 2005. 201(9): p. 1397-405), which were established from adipose tissue from the umbilical region of a donor aged 31 months and from pre-pubic adipose tissue from a donor aged 4 months, respectively (FIG. 8 and results not shown).

Oxygen Consumption and Respiratory Decoupling of hMADS Cells Differentiated into White and Brown Adipocytes One major characteristic of brown adipocytes is an intense respiratory activity and an important decoupling of oxidative phosphorylation. Oxygen consumption, determined using an oxygen-sensitive electrode (Cannon, B. and J. Nedergaard, Physiol Rev, 2004. 84(1): p. 277-359) made it possible to measure relative respiration rates. The results show the significant effect of a long-term treatment with rosiglitazone on total and uncoupled respiratory activities. After 20 days of chronic exposure enabling the acquisition of the brown phenotype, compared with the values obtained with hMADS-2 cells exposed between days 3 and 9 and expressing the white phenotype, these two activities are increased by a factor of 3 and 2.5, respectively (FIGS. 5A and B). When hMADS-2 cells are differentiated beforehand into white adipocytes, and then treated later between days 16 and 20 with rosiglitazone, the increase in total and uncoupled respiratory activities is reduced but remains quite notable (FIGS. 5A and B). An important stimulation of oxygen consumption by a specific β-adrenergic receptor agonist such as isoproterenol is also observed during the acquisition of a brown phenotype (FIG. 5C). These results show that acquisition of the brown phenotype by hMADS-2 cells is accompanied as expected via UCP1 by an increase in oxygen consumption, uncoupling activity and stimulation of respiration by a specific β-adrenergic receptor agonist, demonstrating that the brown adipocytes obtained from hMADS cells are functional.

III. Discussion

The fluorodeoxyglucose-positron-emission technique recently made it possible to show, in healthy adult humans, the presence of active brown adipose tissue in sites distinct from white adipose tissue (Nedergaard, J. et al., Am J Physiol Endocrinol Metab, 2007. 293(2): p. E444-52). Thus, contrary to the consensus that prevailed during recent decades, these important observations suggest the possibility of stimulating the metabolic activity of BAT in order to modulate energy expenditure in man. Indeed, brown adipose tissue in rodents plays an important role in adaptive thermogenesis, its ablation by transgenesis leading to obesity and a dysfunction being observed in obese rodents (Cannon, B. and J. Nedergaard, Physiol Rev, 2004. 84(1): p. 277-359; Lowell, B. B., et al., Nature, 1993. 366(6457): p. 740-2), whereas in man the role of BAT remains a subject of debate (Cinti, S., Nutr Metab Cardiovasc Dis, 2006. 16(8): p. 569-74). Pharmacologically speaking, taking into account all these observations, the development of a model of human brown adipocytes should thus prove to be of utmost importance.

Our results show for the first time that multipotent human stem cells, established from the adipose tissue of young donors and already known to differentiate into white adipocytes (Rodriguez, A. M., et al., Biochem Biophys Res Commun, 2004. 315(2): p. 255-63; Rodriguez, A. M., et al., J Exp Med, 2005. 201(9): p. 1397-405), are also capable of giving rise to brown adipocytes.

Biologically speaking, our results support the hypothesis according to which hMADS cells are immature stem cells whose lineage would be upstream of white and brown lineages. Once engaged in the brown lineage, hMADS cells exhibit all the characteristics of rodent brown adipocytes; they express the UCP1, CIDEA, PGC-1α, PGC-1β and PRDM16 genes as well as three members of the PPAR family. Crucially, acquisition of the brown phenotype is accompanied by an important increase in respiratory and uncoupling activities. The positive modulation of UCP1 expression by isoproterenol and the compound CL316243 demonstrates that the signaling pathway generated by J-adrenergic receptors, in particular β3 receptors, is also functional in these cells.

Up to this date, the presence and role of β3-adrenergic receptors in man has been much debated (Lafontan, M. and M. Berlan, Trends Pharmacol Sci, 2003. 24(6): p. 276-83). Thus, brown adipocytes of young baboons weakly express these receptors but no lipolysis is observed in response to four β3-adrenergic agonists (Viguerie-Bascands, N., et al., J Clin Endocrinol Metab, 1996. 81(1): p. 368-75). In addition, human brown adipocytes immortalized by transgenesis and expressing β3-adrenergic receptors show only weak lipolytic activity in response to CGP12177A, a partial β3 agonist, and these receptors appear only weakly coupled with adenylate cyclase (Zilberfarb, V., et al., J Cell Sci, 1997. 110(Pt 7): p. 801-7; Jockers, R., et al., Endocrinology, 1998. 139(6): p. 2676-84). In both cases, no stimulation of UCP1 expression and no uncoupling respiratory activity have been reported in response to a specific β3 agonist, contrary to the results of our work. Moreover, no stimulation of respiratory activity by a specific β-adrenergic receptor agonist has been reported.

Rosiglitazone belongs to the family of thiazolidinediones, a class of insulin-sensitizing molecules used in the treatment of type 2 diabetes (Olefsky, J. M. and A. R. Saltiel, Trends Endocrinol Metab, 2000. 11(9): p. 362-8). It promotes terminal adipocyte differentiation by specifically activating PPARγ (Rodriguez, A. M., et al., Biochem Biophys Res Commun, 2004. 315(2): p. 255-63; Tai, T. A., et al., J Biol Chem, 1996. 271(47): p. 29909-14; Forman, B. M., et al., Cell, 1995. 83(5): p. 803-12). PPARγ activation occurs in white preadipocytes as well as in brown preadipocytes and leads to their differentiation into white and brown adipocytes, respectively (Nedergaard, J., et al., Biochim Biophys Acta, 2005. 1740(2): p. 293-304; Petrovic, N. et al., Am J Physiol Endocrinol Metab, (May 20, 2008). doi:10.1152/ajpendo.00035.2008).

Notably, in spite of the presence of rosiglitazone and in spite of the fact that activation of the PKA pathway by the DEX/IBMX "cocktail" proves to be indispensable during the first three days of differentiation, this stimulatory effect appears insufficient and only differentiation into white adipocytes occurs. After elimination of DEX/IBMX from the culture medium, it is striking to note that the acquisition of a brown adipocyte phenotype by hMADS cells no longer depends on the duration of activation on PPARγ by rosiglitazone even though PGC-1α, PGC-1β and PRDM16 are already fully expressed in cells expressing the white phenotype.

It is known that in the mouse, PRDM16 induces in white adipocytes the expression of UCP1 although activation of PPARγ is necessary for the expression of CIDEA and mitochondrial components (Seale, P., et al., Cell Metab, 2007. 6(1): p. 38-54). Our results are in agreement with these observations and with the presence of a PPAR response element in the promoter of the CIDEA gene (Viswakarma, N., et al., J Biol Chem, 2007. 282 (25): p. 18613-24). However, it can not be excluded that, beyond the expression of PRDM16, PGC-1α and PGC-1β, a prolonged exposure to rosiglitazone does not induce other molecular events which are also necessary for the full acquisition of a brown phenotype. A differential transcriptomic analysis between hMADS cells treated briefly or for a long time with rosiglitazone should provide answers to this hypothesis.

Rosiglitazone, while normalizing glycemia and insulinemia, leads to an increase in body weight in animals as well as in many patients (Carmona, M. C., et al., Int J Obes (Land), 2005. 29(7): p. 864-71; Goldberg, R. B., Curr Opin Lipidol, 2007. 18(4): p. 435-42; Home, P. D., et al., Diabet Med, 2007. 24(6): p. 626-34; Joosen, A. M., et al., Diabetes Metab Res Rev, 2006. 22(3): p. 204-10). Our results do not exclude the possibility that, in man, it also can, although insufficiently, increase BAT activity observed in a large proportion of healthy individuals (Nedergaard, J. et al., Am J Physiol Endocrinol Metab, 2007. 293(2): p. E444-52; Cypess, A M et al., N. Engl. J. Med. 2009. 360: p. 1509-17; Saito, M. et al., Diabetes 2009. Publish Ahead of Print, Online April 28; van Marken Lichtenbelt, W. et al., N. Engl. J. Med. 2009. 390: p. 1500-08; Virtanen, K A et al., N. Engl. J. Med. 2009. 360: p. 1518-1525).

The contribution of BAT to energy expenditure, in the case of non-shivering thermogenesis or induced by a hypercaloric diet, is well established in rodents. In human, the differences in weight gain observed between individuals appear related to differences in their capacity to increase energy expenditure in response to ingesta (Lowell, B. B and E. S. Bachman, J Biol Chem, 2003. 278(32): p. 29385-8), and the mass of brown adipose tissue is inversely proportional to the mass of white adipose tissue (Saito, M. et al., Diabetes 2009. Publish Ahead of Print, Online April 28; Virtanen, K A et al., N. Engl. J. Med. 2009. 360: p. 1518-1525). If these observations are related to different capacities between individuals to increase the mass and/or the activity of BAT, our model of human brown adipocytes should enable screening for molecules capable of increasing the formation and the functions of BAT, in particular by stimulating PRDM16 expression and respiratory and uncoupling capacities of cells. Among the possibilities, an increase in UCP1 expression could be considered by means of the dual activation of the PKA pathway via β-adrenergic receptors and via the TGR5 receptor activated by biliary salts (Watanabe, M., et al., Nature, 2006. 439(7075): p. 484-9).

IV. Supplementary Results

The materials and methods are those indicated in part I of the Examples section above.

1—Recent work showed in mouse i) the existence of a myogenic signature of brown adipocytes distinct from the one of white adipocytes (Timmons et al., 2007; Seale et al., 2008, Nature 454:961-967) and ii) the possibility to generate brown adipocytes from white precursors by treatment with Bone Morphogentic Protein 7 (BMP7) (Tseng et al., 2008. Nature 454:1000-1004) or by transgenesis (Tiraby, C. et al., J. Biol. Chem. 2003. 278: p. 33370-76).

We have shown that our human hMADS cells do not have a muscle signature since they do not express the Myf5 gene neither during the proliferation phase, nor during or after their differentiation into adipose cells as in osseous cells.

Moreover, treatment of hMADS cells with BMP7 alone does not enable their differentiation into adipocytes in the absence of rosiglitazone, but rather leads to a weak increase in UCP-1 protein expression in cells differentiated beforehand into white adipocytes.

2—The effects of rosiglitazone on the hMADS cells differentiation into white and brown adipocytes are mediated by the nuclear receptor PPARγ. Indeed, adding a PPARγ antagonist, the compound GW 9662, to the differentiation medium prevents on the one hand the differentiation of hMADS cells into adipocytes, and on the other hand does not allow expression of the UCP-1 gene in cells differentiated beforehand into white adipocytes.

3—Compared with white adipocytes, brown adipocytes exhibit a very strong mitochondriogenesis. We showed that the level of mRNA coding for mitochondrial carnitine palmitoyltransferase (CTP1B) is strongly increased when hMADS-2 cells switch from the white phenotype to the brown phenotype. Recent results show that the cytochrome c oxidase activity (marker of the inner mitochondrial membrane) is also increased in brown hMADS adipocytes compared with white adipocytes, thus strengthening our observations regarding the increase in mitochondriogenesis during the transition from the white phenotype to the brown phenotype.

4—In rodents, biliary acids from intestinal reabsorption bind to a receptor coupled with G proteins (TGR5) located on the plasma membrane of brown adipocytes. The production of cAMP stimulates the expression of type II iodothyronine deiodinase which increases the intracellular concentrations of T3. The latter then stimulate mitochondrial decoupling via UCP and the dissipation of energy in the form of heat (Watanabe et al., 2006). In human, such a system has never been described. hMADS cells express the TGR5 gene during adipocyte differentiation thus making it possible to consider pharmacological studies on respiration decoupling using TGR5 receptor agonist ligands.

BIBLIOGRAPHICAL REFERENCES

Ailhaud, G., Grimaldi, P., and Negrel, R. (1992). Cellular and molecular aspects of adipose tissue development. Annu Rev Nutr 12, 207-233.

Bezy, O., Elabd, C., Cochet, O., Petersen, R. K., Kristiansen, K., Dani, C., Ailhaud, G., and Amri, E. Z. (2005). Delta-interacting protein A, a new inhibitory partner of CCAAT/enhancer-binding protein beta, implicated in adipocyte differentiation. J Biol Chem 280, 11432-11438.

Bogacka, I., Xie, H., Bray, G. A., and Smith, S. R. (2005). Pioglitazone induces mitochondrial biogenesis in human subcutaneous adipose tissue in vivo. Diabetes 54, 1392-1399.

Briscini, L., Tonello, C., Dioni, L., Carruba, M. O., and Nisoli, E. (1998). Bcl-2 and Bax are involved in the sympathetic protection of brown adipocytes from obesity-linked apoptosis. FEBS Lett 431, 80-84.

Cannon, B., and Nedergaard, J. (2004). Brown adipose tissue: function and physiological significance. Physiol Rev 84, 277-359.

Carmona, M. C., Louche, K., Nibbelink, M., Prunet, B., Bross, A., Desbazeille, M., Dacquet, C., Renard, P., Casteilla, L., and Penicaud, L. (2005). Fenofibrate prevents Rosiglitazone-induced body weight gain in ob/ob mice. Int J Obes (Lond) 29, 864-871.

Casteilla, L., Champigny, O., Bouillaud, F., Robelin, J., and Ricquier, D. (1989). Sequential changes in the expression of mitochondrial protein mRNA during the development of brown adipose tissue in bovine and ovine species. Sudden occurrence of uncoupling protein mRNA during embryogenesis and its disappearance after birth. Biochem J 257, 665-671.

Casteilla, L., Forest, C., Robelin, J., Ricquier, D., Lombet, A., and Ailhaud, G. (1987). Characterization of mitochondrial-uncoupling protein in bovine fetus and newborn calf. Am J Physiol 252, E627-636.

Casteilla, L., Nougues, J., Reyne, Y., and Ricquier, D. (1991). Differentiation of ovine brown adipocyte precursor cells in a chemically defined serum-free medium. Importance of glucocorticoids and age of animals. Eur J Biochem 198, 195-199.

Cinti, S. (2006). The role of brown adipose tissue in human obesity. Nutr Metab Cardiovasc Dis 16, 569-574.

Cousin, B., Cinti, S., Morroni, M., Raimbault, S., Ricquier, D., Penicaud, L., and Casteilla, L. (1992). Occurrence of brown adipocytes in rat white adipose tissue: molecular and morphological characterization. J Cell Sci 103 (Pt 4), 931-942.

Cypess, A. M., Lehman, S., Williams, G., Tal, I., Rodman, D., Goldfine, A. B., Kuo, F. C., Palmer, E. L., Tseng, Y. H., Doria, A., Kolodny, G. M., and Kahn, C. R. (2009). Identification and importance of brown adipose tissue in adult humans. N Engl J Med 360, 1509-1517.

Elabd, C., Chiellini, C., Massoudi, A., Cochet, O., Zaragosi, L. E., Trojani, C., Michiels, J. F., Weiss, P., Carle, G., Rochet, N., et al. (2007). Human adipose tissue-derived multipotent stem cells differentiate in vitro and in vivo into osteocyte-like cells. Biochem Biophys Res Commun 361, 342-348.

Foellmi-Adams, L. A., Wyse, B. M., Herron, D., Nedergaard, J., and Kletzien, R. F. (1996). Induction of uncoupling protein in brown adipose tissue. Synergy between norepinephrine and pioglitazone, an insulin-sensitizing agent. Biochem Pharmacol 52, 693-701.

Forman, B. M., Tontonoz, P., Chen, J., Brun, R. P., Spiegelman, B. M., and Evans, R. M. (1995). 15-Deoxy-delta12,14-prostaglandin J2 is a ligand for the adipocyte determination factor PPAR gamma. Cell 83, 803-812.

Fukui, Y., Masui, S., Osada, S., Umesono, K., and Motojima, K. (2000). A new thiazolidinedione, NC-2100, which is a weak PPAR-gamma activator, exhibits potent antidiabetic effects and induces uncoupling protein 1 in white adipose tissue of KKAy obese mice. Diabetes 49, 759-767.

Garruti, G., and Ricquier, D. (1992). Analysis of uncoupling protein and its mRNA in adipose tissue deposits of adult humans. Int J Obes Relat Metab Disord 16, 383-390.

Goldberg, R. B. (2007). The new clinical trials with thiazolidinediones—DREAM, ADOPT, and CHICAGO: promises fulfilled? Curr Opin Lipidol 18, 435-442.

Home, P. D., Jones, N. P., Pocock, S. J., Beck-Nielsen, H., Gomis, R., Hanefeld, M., Komajda, M., and Curtis, P. (2007). Rosiglitazone RECORD study: glucose control outcomes at 18 months. Diabet Med 24, 626-634.

Jockers, R., Issad, T., Zilberfarb, V., de Coppet, P., Marullo, S., and Strosberg, A. D. (1998). Desensitization of the beta-adrenergic response in human brown adipocytes. Endocrinology 139, 2676-2684.

Joosen, A. M., Bakker, A. H., Gering, M. J., and Westerterp, K. R. (2006). The effect of the PPARgamma ligand rosiglitazone on energy balance regulation. Diabetes Metab Res Rev 22, 204-210.

Kelly, L. J., Vicario, P. P., Thompson, G. M., Candelore, M. R., Doebber, T. W., Ventre, J., Wu, M. S., Meurer, R., Forrest, M. J., Conner, M. W., et al. (1998). Peroxisome proliferator-activated receptors gamma and alpha mediate in vivo regulation of uncoupling protein (UCP-1, UCP-2, UCP-3) gene expression. Endocrinology 139, 4920-4927.

Lafontan, M., and Berlan, M. (2003). Do regional differences in adipocyte biology provide new pathophysiological insights? Trends Pharmacol Sci 24, 276-283.

Lindquist, J. M., and Rehnmark, S. (1998). Ambient temperature regulation of apoptosis in brown adipose tissue. Erk1/2 promotes norepinephrine-dependent cell survival. J Biol Chem 273, 30147-30156.

Lowell, B. B., and Bachman, E. S. (2003). Beta-Adrenergic receptors, diet-induced thermogenesis, and obesity. J Biol Chem 278, 29385-29388.

Lowell, B. B., V, S. S., Hamann, A., Lawitts, J. A., Himms-Hagen, J., Boyer, B. B., Kozak, L. P., and Flier, J. S. (1993). Development of obesity in transgenic mice after genetic ablation of brown adipose tissue. Nature 366, 740-742.

Mercer, S. W., and Trayhurn, P. (1986). Effects of ciglitazone on insulin resistance and thermogenic responsiveness to acute cold in brown adipose tissue of genetically obese (ob/ob) mice. FEBS Lett 195, 12-16.

Moulin, K., Truel, N., Andre, M., Arnauld, E., Nibbelink, M., Cousin, B., Dani, C., Penicaud, L., and Casteilla, L. (2001). Emergence during development of the white-adipocyte cell phenotype is independent of brown-adipocyte cell phenotype. Biochem J 356, 659-664.

Nedergaard, J., Bengtsson, T., and Cannon, B. (2007). Unexpected evidence for active brown adipose tissue in adult humans. Am J Physiol Endocrinol Metab 293, E444-452.

Nedergaard, J., Petrovic, N., Lindgren, E. M., Jacobsson, A., and Cannon, B. (2005). PPARgamma in the control of brown adipocyte differentiation. Biochim Biophys Acta 1740, 293-304.

Negrel, R., Grimaldi, P., and Ailhaud, G. (1978). Establishment of preadipocyte clonal line from epididymal fat pad of ob/ob mouse that responds to insulin and to lipolytic hormones. Proc Natl Acad Sci USA 75, 6054-6058.

Nisoli, E., Cardile, A., Bulbarelli, A., Tedesco, L., Bracale, R., Cozzi, V., Morroni, M., Cinti, S., Valerio, A., and Carruba, M. O. (2006). White adipocytes are less prone to apoptotic stimuli than brown adipocytes in rodent. Cell Death Differ 13, 2154-2156.

Olefsky, J. M., and Saltiel, A. R. (2000). PPAR gamma and the treatment of insulin resistance. Trends Endocrinol Metab 11, 362-368.

Papineau, D., Gagnon, A., and Sorisky, A. (2003). Apoptosis of human abdominal preadipocytes before and after differentiation into adipocytes in culture. Metabolism 52, 987-992.

Petrovic, N., Shabalina, I. G., Timmons, J. A., Cannon, B., and Nedergaard, J. (2008). Thermogenically Competent Non-Adrenergic Recruitment in Brown Predipocytes by a PPAR{gamma} Agonist. Am J Physiol Endocrinol Metab.

Puigserver, P., Rhee, J., Lin, J., Wu, Z., Yoon, J. C., Zhang, C. Y., Krauss, S., Mootha, V. K., Lowell, B. B., and Spiegelman, B. M. (2001). Cytokine stimulation of energy expenditure through p38 MAP kinase activation of PPAR-gamma coactivator-1. Mol Cell 8, 971-982.

Rodriguez, A. M., Elabd, C., Delteil, F., Astier, J., Vernochet, C., Saint-Marc, P., Guesnet, J., Guezennec, A., Amri, E. Z., Dani, C., et al. (2004). Adipocyte differentiation of multipotent cells established from human adipose tissue. Biochem Biophys Res Commun 315, 255-263.

Rodriguez, A. M., Pisani, D., Dechesne, C. A., Turc-Carel, C., Kurzenne, J. Y., Wdziekonski, B., Villageois, A., Bagnis, C., Breittmayer, J. P., Groux, H., et al. (2005). Transplantation of a multipotent cell population from human adipose tissue induces dystrophin expression in the immunocompetent mdx mouse. J Exp Med 201, 1397-1405.

Rosen, E. D., and Spiegelman, B. M. (2006). Adipocytes as regulators of energy balance and glucose homeostasis. Nature 444, 847-853.

Saito, M., Okamatsu-Ogura, Y., Matsushita, M., Watanabe, K., Yoneshiro, T., Nio-Kobayashi, J., Iwanaga, T., Miyagawa, M., Kameya, T., Nakada, K., Kawai, Y., and Tsujisaki, M. (2009). High Incidence of Metabolically Active Brown Adipose Tissue in Healthy Adult Humans Effects of Cold Exposure and Adiposity. Diabetes.

Seale, P., Kajimura, S., Yang, W., Chin, S., Rohas, L. M., Uldry, M., Tavernier, G., Langin, D., and Spiegelman, B. M. (2007). Transcriptional Control of Brown Fat Determination by PRDM16. Cell Metab 6, 38-54.

Seale, P., Bjork, B., Yang, W., Kajimura, S., Chin, S., Kuang, S., Scime, A., Devarakonda, S., Conroe, H. M., Erdjument-Bromage, H., et al. 2008. PRDM16 controls a brown fat/skeletal muscle switch. Nature 454, 961-967.

Tai, T. A., Jennermann, C., Brown, K. K., Oliver, B. B., MacGinnitie, M. A., Wilkison, W. O., Brown, H. R., Lehmann, J. M., Kliewer, S. A., Morris, D. C., et al. (1996). Activation of the nuclear receptor peroxisome proliferator-activated receptor gamma promotes brown adipocyte differentiation. J Biol Chem 271, 29909-29914.

Timmons, J. A., Wennmalm, K., Larsson, O., Walden, T. B., Lassmann, T., Petrovic, N., Hamilton, D. L., Gimeno, R. E., Wahlestedt, C., Baar, K., et al. (2007). Myogenic gene expression signature establishes that brown and white adipocytes originate from distinct cell lineages. Proc Natl Acad Sci USA 104, 4401-4406.

Tiraby, C., and Langin, D. (2003). Conversion from white to brown adipocytes: a strategy for the control of fat mass? Trends Endocrinol Metab 14, 439-441.

Tiraby, C., Tavernier, G., Lefort, C., Larrouy, D., Bouillaud, F., Ricquier, D., and Langin, D. (2003). Acquirement of brown fat cell features by human white adipocytes. J Biol Chem 278, 33370-33376.

Tseng, Y. H., Kokkotou, E., Schulz, T. J., Huang, T. L., Winnay, J. N., Taniguchi, C. M., Tran, T. T., Suzuki, R., Espinoza, D. O., Yamamoto, Y., et al. 2008. New role of bone morphogenetic protein 7 in brown adipogenesis and energy expenditure. Nature 454, 1000-1004.

Uldry, M., Yang, W., St-Pierre, J., Lin, J., Seale, P., and Spiegelman, B. M. (2006). Complementary action of the PGC-1 coactivators in mitochondrial biogenesis and brown fat differentiation. Cell Metab 3, 333-341.

van Marken Lichtenbelt, W. D., Vanhommerig, J. W., Smulders, N. M., Drossaerts, J. M., Kemerink, G. J., Bouvy, N. D., Schrauwen, P., and Teule, G. J. (2009). Cold-activated brown adipose tissue in healthy men. N Engl J Med 360, 1500-1508.

Viguerie-Bascands, N., Bousquet-Melou, A., Galitzky, J., Larrouy, D., Ricquier, D., Berlan, M., and Casteilla, L. (1996). Evidence for numerous brown adipocytes lacking functional beta 3-adrenoceptors in fat pads from nonhuman primates. J Clin Endocrinol Metab 81, 368-375.

Virtanen, K. A., Lidell, M. E., Orava, J., Heglind, M., Westergren, R., Niemi, T., Taittonen, M., Laine, J., Savisto, N. J., Enerback, S., and Nuutila, P. (2009). Functional brown adipose tissue in healthy adults. N Engl J Med 360, 1518-1525.

Viswakarma, N., Yu, S., Naik, S., Kashireddy, P., Matsumoto, K., Sarkar, J., Surapureddi, S., Jia, Y., Rao, M. S., and Reddy, J. K. (2007). Transcriptional regulation of Cidea, mitochondrial cell death-inducing DNA fragmentation factor alpha-like effector A, in mouse liver by peroxisome proliferator-activated receptor alpha and gamma. J Biol Chem 282, 18613-18624.

Watanabe, M., Houten, S. M., Mataki, C., Christoffolete, M. A., Kim, B. W., Sato, H., Messaddeq, N., Harney, J. W., Ezaki, O., Kodama, T., et al. (2006). Bile acids induce energy expenditure by promoting intracellular thyroid hormone activation. Nature 439, 484-489.

Wilson-Fritch, L., Nicoloro, S., Chouinard, M., Lazar, M. A., Chui, P. C., Leszyk, J., Straubhaar, J., Czech, M. P., and Corvera, S. (2004). Mitochondrial remodeling in adipose tissue associated with obesity and treatment with rosiglitazone. J Clin Invest 114, 1281-1289.

Xue, B., Coulter, A., Rim, J. S., Koza, R. A., and Kozak, L. P. (2005). Transcriptional synergy and the regulation of Ucp1 during brown adipocyte induction in white fat depots. Mol Cell Biol 25, 8311-8322.

Zaragosi, L. E., Ailhaud, G., and Dani, C. (2006). Autocrine fibroblast growth factor 2 signaling is critical for self-renewal of human multipotent adipose-derived stem cells. Stem Cells 24, 2412-2419.

Zhou, Z., Yon Toh, S., Chen, Z., Guo, K., Ng, C. P., Ponniah, S., Lin, S. C., Hong, W., and Li, P. (2003). Cidea-deficient mice have lean phenotype and are resistant to obesity. Nat Genet. 35, 49-56.

Zilberfarb, V., Pietri-Rouxel, F., Jockers, R., Krief, S., Delouis, C., Issad, T., and Strosberg, A. D. (1997). Human immortalized brown adipocytes express functional beta3-adrenoceptor coupled to lipolysis. J Cell Sci 110 (Pt 7), 801-807.

The invention claimed is:

1. A method for differentiating a population of human multipotent adipose-derived stem cells (hMADs cells) into a functional human brown adipocytes population, comprising the steps of:
   a) culturing the hMADs cells in a first differentiation medium consisting essentially of nutrients, transferrin, dexamethasone (DEX), isobutylmethylxanthine (IBMX), insulin, and T3 for a duration period comprised between 2 and 4 days, thereby initiating the differentiation of the hMADs cells; and
   b) culturing the cells from step a) in a second differentiation medium comprising nutrients, transferrin, insulin, T3 and a specific PPAR gamma agonist for 30 days, thereby differentiating the cells from step a) into functional human brown adipocytes,
   wherein the second differentiation medium does not comprise DEX or IBMX.

2. The method for differentiating according to claim 1, wherein the specific PPAR gamma agonist is a thiazolidinedione selected from the group consisting of rosiglitazone, ciglitazone, pioglitazone, darglitazone and troglitazone.

3. The method for differentiating according to claim 2, wherein a concentration of the specific PPAR gamma agonist is between 5 nM and 1,000 nM when the agonist is rosiglitazone, between 0.2 µM and 10 µM when the agonist is pioglitazone, between 0.5 µM and 20 µM when the agonist is ciglitazone, between 0.2 µM and 20 µM when the agonist is darglitazone and between 0.2 µm and 10 µM when the agonist is troglitazone.

4. The method for differentiating according to claim 1, further comprising verification of functionality of the human brown adipocytes population obtained after differentiating the hMADS cells population, said verification comprising the following successive steps:
   c) stimulating the respiratory activity of said human brown adipocytes population by culturing said population with a specific β-adrenergic receptor agonst,
   d) quantifying expression of a gene encoding uncoupling protein 1 (UCP1) and of oxygen consumption, and
   e) verifying that said population is functional when the expression of the gene encoding uncoupling protein 1 (UCP1) and/or the oxygen consumption is increased compared with the one obtained in the absence of stimulation by the specific β-adrenergic receptor agonist.

5. The method for differentiating according to claim 4, wherein the specific β-adrenergic receptor agonist is selected from isoproterenol, noradrenaline, adrenaline, dobutamine, terbutaline and compound CL316243.

6. The method for differentiating according to claim 4, wherein a concentration of the specific β-adrenergic receptor agonist is between 1 nM and 1,000 nM.

7. A method for converting a human white adipocytes population into a functional human brown adipocytes population, comprising the steps of:
   a) culturing said human white adipocytes population in a differentiation medium comprising nutrients, transferrin, insulin, T3 and a specific PPAR gamma agonist, for a duration period comprised between 1 and 10 days, thereby converting the human white adipocytes into functional human brown adipocytes,
   wherein the differentiation medium does not comprise dexamethasone (DEX) or isobutylmethylxanthine (IBMX).

8. The method for converting according to claim 7, wherein the specific PPAR gamma agonist is a thiazolidinedione, said thiazolidinedione selected from the group consisting of rosiglitazone, ciglitazone, pioglitazone, darglitazone and troglitazone.

9. The method for converting according to claim 8, wherein a concentration of the specific PPAR gamma agonist is between 5 nM and 1,000 nM when the agonist is rosiglitazone, between 0.2 µM and 10 µM when the agonist is pioglitazone, between 0.5 µM and 20 µM when the agonist is ciglitazone, between 0.2 µm and 20 µM when the agonist is darglitazone and between 0.2 µM and 10 µM when the agonist is troglitazone.

10. The method for converting according to claim 7, further comprising verification of functionality of the human brown adipocytes population obtained after converting the human white adipocytes population, said verification comprising the following successive steps:
   b) stimulating the respiratory activity of said human brown adipocytes population by culturing said population with a specific β-adrenergic receptor agonist,
   c) quantifying expression of a gene encoding for uncoupling protein 1 (UCP1) and of oxygen consumption, and
   d) verifying that said population is functional when the expression of the gene encoding uncoupling protein 1 (UCP1) and/or the oxygen consumption is increased compared with the one obtained in the absence of stimulation by the specific β-adrenergic receptor agonist.

11. The method for converting according to claim 10, wherein the specific β-adrenergic receptor agonist is selected from isoproterenol, noradrenaline, adrenaline, dobutamine, terbutaline and compound CL316243.

12. The method for converting according to claim 10, wherein a concentration of the specific β-adrenergic receptor agonist is between 1 nM and 1,000 nM.

13. A method for differentiating a population of human multipotent adipose-derived stem cells (hMADS cells) into a functional human brown adipocytes population, comprising the steps of:
   a) culturing the hMADs cells in a first differentiation medium comprising dexamethasone (DEX), isobutylmethylxanthine (IBMX), insulin, and T3 for a duration period comprised between 2 and 4 days, thereby initiating the differentiation of the hMADs cells;
   b) culturing the cells from step a) in a second differentiation medium comprising insulin, T3 and a first specific PPAR gamma agonist for a duration period comprised between 2 and 9 days, thereby differentiating the cells from step a) into white adipocytes;
   c) culturing the white adipocytes from step b) for a duration period comprised between 2 to 10 days without the stimulation of differentiation with a PPAR gamma agonist, and
   d) culturing the cells from step c) for a duration period comprised between 1 and 10 days, in a third differentiation medium comprising insulin, T3 and a second specific PPAR gamma agonist, thereby differentiating the cells from step c) into functional human brown adipocytes,
   wherein the first and second PPARγ gamma agonists may be the same or different, and
   wherein the second differentiation medium and the third differentiation medium do not comprise the DEX or the IBMX.

14. The method for differentiating according to claim 13, wherein the first and/or second specific PPAR gamma agonist is a thiazolidinedione selected from the group consisting of rosiglitazone, ciglitazone, pioglitazone, darglitazone and troglitazone.

15. The method for differentiating according to claim 14, wherein a concentration of the first and/or second specific PPAR gamma agonist is between 5 nM and 1,000 nM when the agonist is rosiglitazone, between 0.2 µM and 10 µM when the agonist is pioglitazone, between 0.5 µM and 20 µM when the agonist is ciglitazone, between 0.2 µM and 20 µM when the agonist is darglitazone and between 0.2 µm and 10 µM when the agonist is troglitazone.

16. The method for differentiating according to claim 13, further comprising verification of functionality of the human brown adipocytes population obtained after differentiating the hMADS cells population, said verification comprising the following successive steps:

e) stimulating the respiratory activity of said human brown adipocytes population by culturing said population with a specific β-adrenergic receptor agonist, f) quantifying expression of a gene encoding uncoupling protein 1 (UCP1) and of oxygen consumption, and g) verifying that said population is functional when the expression of the gene encoding uncoupling protein 1 (UCP1) and/or the oxygen consumption is increased compared with the one obtained in the absence of stimulation by the specific β-adrenergic receptor agonist.

17. The method for differentiating according to claim 16, wherein the specific β-adrenergic receptor agonist is selected from isoproterenol, noradrenaline, adrenaline, dobutamine, terbutaline and compound CL316243.

18. The method for differentiating according to claim 16, wherein a concentration of specific β-adrenergic receptor agonist is between 1 nM and 1,000 nM.

\* \* \* \* \*

SEQUENCE LISTING

```
<160> NUMBER OF SEQ ID NOS: 28

<210> SEQ ID NO 1
<211> LENGTH: 21
<212> TYPE: DNA
<213> ORGANISM: artificial
<220> FEATURE:
<223> OTHER INFORMATION: FABP4 sense primer

<400> SEQUENCE: 1
tgtgcagaaa tgggatggaa a                                          21

<210> SEQ ID NO 2
<211> LENGTH: 21
<212> TYPE: DNA
<213> ORGANISM: artificial
<220> FEATURE:
<223> OTHER INFORMATION: FABP4 anti-sense primer

<400> SEQUENCE: 2
caacgtccct tggcttatgc t                                          21

<210> SEQ ID NO 3
<211> LENGTH: 20
<212> TYPE: DNA
<213> ORGANISM: artificial
<220> FEATURE:
<223> OTHER INFORMATION: UCP-1 sense primer
```

```
<400> SEQUENCE: 3
gtgtgcccaa ctgtgcaatg                                                   20

<210> SEQ ID NO 4
<211> LENGTH: 20
<212> TYPE: DNA
<213> ORGANISM: artificial
<220> FEATURE:
<223> OTHER INFORMATION: UCP-1 anti-sense primer

<400> SEQUENCE: 4
ccaggatcca agtcgcaaga                                                   20

<210> SEQ ID NO 5
<211> LENGTH: 21
<212> TYPE: DNA
<213> ORGANISM: artificial
<220> FEATURE:
<223> OTHER INFORMATION: UCP-2 sense primer

<400> SEQUENCE: 5
ggcctcaccg tgagaccttac                                                  21

<210> SEQ ID NO 6
<211> LENGTH: 19
<212> TYPE: DNA
<213> ORGANISM: artificial
<220> FEATURE:
<223> OTHER INFORMATION: UCP-2 anti-sense primer

<400> SEQUENCE: 6
tggccttgaa cccaaccat                                                    19

<210> SEQ ID NO 7
<211> LENGTH: 21
<212> TYPE: DNA
<213> ORGANISM: artificial
<220> FEATURE:
<223> OTHER INFORMATION: PPAR gamma sense primer

<400> SEQUENCE: 7
agcctcatga agagccttcc a                                                 21

<210> SEQ ID NO 8
<211> LENGTH: 19
<212> TYPE: DNA
<213> ORGANISM: artificial
<220> FEATURE:
<223> OTHER INFORMATION: PPAR gamma anti-sense primer

<400> SEQUENCE: 8
tccggaagaa acccttgca                                                    19

<210> SEQ ID NO 9
<211> LENGTH: 20
<212> TYPE: DNA
<213> ORGANISM: artificial
<220> FEATURE:
<223> OTHER INFORMATION: PPAR alpha sense primer

<400> SEQUENCE: 9
ggcgaacgat tcgactcaag                                                   20

<210> SEQ ID NO 10
<211> LENGTH: 20
```

```
<212> TYPE: DNA
<213> ORGANISM: artificial
<220> FEATURE:
<223> OTHER INFORMATION: PPAR alpha anti-sense primer

<400> SEQUENCE: 10
tccaaaacga atcgcgttgt                                              20

<210> SEQ ID NO 11
<211> LENGTH: 24
<212> TYPE: DNA
<213> ORGANISM: artificial
<220> FEATURE:
<223> OTHER INFORMATION: PGC-1 alpha sense primer

<400> SEQUENCE: 11
ctgtgtcacc acccaaatcc ttat                                         24

<210> SEQ ID NO 12
<211> LENGTH: 22
<212> TYPE: DNA
<213> ORGANISM: artificial
<220> FEATURE:
<223> OTHER INFORMATION: PGC-1 alpha anti-sense primer

<400> SEQUENCE: 12
tgtgtcgaga aaaggacctt ga                                           22

<210> SEQ ID NO 13
<211> LENGTH: 22
<212> TYPE: DNA
<213> ORGANISM: artificial
<220> FEATURE:
<223> OTHER INFORMATION: PGC-1 beta sense primer

<400> SEQUENCE: 13
gcgagaagta cggcttcatc ac                                           22

<210> SEQ ID NO 14
<211> LENGTH: 20
<212> TYPE: DNA
<213> ORGANISM: artificial
<220> FEATURE:
<223> OTHER INFORMATION: PGC-1 beta anti-sense primer

<400> SEQUENCE: 14
cagcgccctt tgtcaaagag                                              20

<210> SEQ ID NO 15
<211> LENGTH: 27
<212> TYPE: DNA
<213> ORGANISM: artificial
<220> FEATURE:
<223> OTHER INFORMATION: PRDM16 sense primer

<400> SEQUENCE: 15
gaaactttat tgccaatagt gagatga                                      27

<210> SEQ ID NO 16
<211> LENGTH: 19
<212> TYPE: DNA
<213> ORGANISM: artificial
<220> FEATURE:
<223> OTHER INFORMATION: PRDM16 anti-sense primer

<400> SEQUENCE: 16
```

```
ccgtccacga tctgcatgt                                                  19
```

<210> SEQ ID NO 17
<211> LENGTH: 18
<212> TYPE: DNA
<213> ORGANISM: artificial
<220> FEATURE:
<223> OTHER INFORMATION: Beta 3-AR sense primer

<400> SEQUENCE: 17

```
gccttcgcct ccaacatg                                                   18
```

<210> SEQ ID NO 18
<211> LENGTH: 22
<212> TYPE: DNA
<213> ORGANISM: artificial
<220> FEATURE:
<223> OTHER INFORMATION: Beta 3-AR anti-sense primer

<400> SEQUENCE: 18

```
agcatcacga gaagaggaag gt                                              22
```

<210> SEQ ID NO 19
<211> LENGTH: 20
<212> TYPE: DNA
<213> ORGANISM: artificial
<220> FEATURE:
<223> OTHER INFORMATION: CIDEA sense primer

<400> SEQUENCE: 19

```
ggcaggttca cgtgtggata                                                 20
```

<210> SEQ ID NO 20
<211> LENGTH: 23
<212> TYPE: DNA
<213> ORGANISM: artificial
<220> FEATURE:
<223> OTHER INFORMATION: CIDEA anti-sense primer

<400> SEQUENCE: 20

```
gaaacacagt gtttggctca aga                                             23
```

<210> SEQ ID NO 21
<211> LENGTH: 18
<212> TYPE: DNA
<213> ORGANISM: artificial
<220> FEATURE:
<223> OTHER INFORMATION: CPT1B sense primer

<400> SEQUENCE: 21

```
aaacagtgcc aggcggtc                                                   18
```

<210> SEQ ID NO 22
<211> LENGTH: 17
<212> TYPE: DNA
<213> ORGANISM: artificial
<220> FEATURE:
<223> OTHER INFORMATION: CPT1B anti-sense primer

<400> SEQUENCE: 22

```
cgtctgccaa cgccttg                                                    17
```

<210> SEQ ID NO 23
<211> LENGTH: 22
<212> TYPE: DNA
<213> ORGANISM: artificial

```
<220> FEATURE:
<223> OTHER INFORMATION: Bax sense primer

<400> SEQUENCE: 23
tgcctcagga tgcgtccacc aa                                              22

<210> SEQ ID NO 24
<211> LENGTH: 25
<212> TYPE: DNA
<213> ORGANISM: artificial
<220> FEATURE:
<223> OTHER INFORMATION: Bax anti-sense primer

<400> SEQUENCE: 24
cggcaatcat cctctgcagc tccat                                           25

<210> SEQ ID NO 25
<211> LENGTH: 17
<212> TYPE: DNA
<213> ORGANISM: artificial
<220> FEATURE:
<223> OTHER INFORMATION: Bcl-2 sense primer

<400> SEQUENCE: 25
gcccccgttg cttttcc                                                    17

<210> SEQ ID NO 26
<211> LENGTH: 22
<212> TYPE: DNA
<213> ORGANISM: artificial
<220> FEATURE:
<223> OTHER INFORMATION: Bcl-2 anti-sense primer

<400> SEQUENCE: 26
ccggttatcg taccctgttc tc                                              22

<210> SEQ ID NO 27
<211> LENGTH: 20
<212> TYPE: DNA
<213> ORGANISM: artificial
<220> FEATURE:
<223> OTHER INFORMATION: TBP sense primer

<400> SEQUENCE: 27
cacgaaccac ggcactgatt                                                 20

<210> SEQ ID NO 28
<211> LENGTH: 22
<212> TYPE: DNA
<213> ORGANISM: artificial
<220> FEATURE:
<223> OTHER INFORMATION: TBP anti-sense primer

<400> SEQUENCE: 28
ttttcttgct gccagtctgg ac                                              22
```